US009790474B2

(12) United States Patent
Sellers

(10) Patent No.: US 9,790,474 B2
(45) Date of Patent: Oct. 17, 2017

(54) ATTENUATION OF INFECTIOUS BRONCHITIS VIRUS VARIANT GA-13

(71) Applicant: UNIVERSITY OF GEORGIA RESEARCH FOUNDATION, INC., Athens, GA (US)

(72) Inventor: Holly S. Sellers, Watkinsville, GA (US)

(73) Assignee: University of Georgia Research Foundation, Inc., Athens, GA (US)

( * ) Notice: Subject to any disclaimer, the term of this patent is extended or adjusted under 35 U.S.C. 154(b) by 0 days.

(21) Appl. No.: 14/808,225

(22) Filed: Jul. 24, 2015

(65) Prior Publication Data

US 2016/0032253 A1    Feb. 4, 2016

Related U.S. Application Data

(60) Provisional application No. 62/028,435, filed on Jul. 24, 2014.

(51) Int. Cl.
  *C12N 7/00*      (2006.01)
  *A61K 39/12*     (2006.01)
  *C07K 14/005*    (2006.01)
  *A61K 39/00*     (2006.01)

(52) U.S. Cl.
  CPC .............. *C12N 7/00* (2013.01); *A61K 39/12* (2013.01); *C07K 14/005* (2013.01); *A61K 2039/5254* (2013.01); *A61K 2039/541* (2013.01); *A61K 2039/552* (2013.01); *C12N 2770/20021* (2013.01); *C12N 2770/20022* (2013.01); *C12N 2770/20034* (2013.01); *C12N 2770/20064* (2013.01)

(58) Field of Classification Search
  None
  See application file for complete search history.

(56) References Cited

U.S. PATENT DOCUMENTS 8,679,504 B2    3/2014    Sellers et al.

FOREIGN PATENT DOCUMENTS

WO    WO 2009/143332 A2    11/2009

OTHER PUBLICATIONS

National Center for Biotechnology Information, National Library of Medicine, National Institutes of Health, GenBank Locus AF027511, Accession No. AF027511, "Avian infectious bronchitis virus CV-1686 spike glycoprotein S1 subunit gene, partial cds" [online]. Bethesda, MD [retrieved on Aug. 4, 2016]. Retrieved from the Internet: <URL: http://www.ncbi.nlm.nih.gov/nuccore/AF027511>; 2 pgs.

National Center for Biotechnology Information, National Library of Medicine, National Institutes of Health, GenBank Locus AF274435, Accession No. AF274435, "Avian infectious bronchitis virus DE072 vaccine spike glycoprotein S1 subunit (spike) gene, partial cds" [online]. Bethesda, MD [retrieved on Aug. 4, 2016]. Retrieved from the Internet: <URL: http://www.ncbi.nlm.nih.gov/nuccore/AF274435>; 2 pgs.

National Center for Biotechnology Information, National Library of Medicine, National Institutes of Health, GenBank Locus AF274436, Accession No. AF274436, "Avian infectious bronchitis virus AR/6386/97 spike glycoprotein S1 subunit (spike) gene, partial cds" [online]. Bethesda, MD [retrieved on Aug. 4, 2016]. Retrieved from the Internet: <URL: http://www.ncbi.nlm.nih.gov/nuccore/AF274436>; 2 pgs.

National Center for Biotechnology Information, National Library of Medicine, National Institutes of Health, GenBank Locus AF274438, Accession No. AF274438, "Avian infectious bronchitis virus GA/2787/98 spike glycoprotein S1 subunit (spike) gene, partial cds" [online]. Bethesda, MD [retrieved on Aug. 4, 2016]. Retrieved from the Internet: <URL: http://www.ncbi.nlm.nih.gov/nuccore/AF274438>; 2 pgs.

National Center for Biotechnology Information, National Library of Medicine, National Institutes of Health, GenBank Locus AF305595, Accession No. AF305595, "Avian infectious bronchitis virus isolate PA/Wolgemuth/98 spike glycoprotein S1 subunit gene, partial cds" [online]. Bethesda, MD [retrieved on Aug. 1, 2016]. Retrieved from the Internet: <URL: http://www.ncbi.nlm.nih.gov/nuccore/AF305595>; 2 pgs.

National Center for Biotechnology Information, National Library of Medicine, National Institutes of Health, GenBank Locus AF338717, Accession No. AF338717, "Avian infectious bronchitis virus GA/7994/99 spike protein (S1) gene, partial cds" [online]. Bethesda, MD [retrieved on Aug. 4, 2016]. Retrieved from the Internet: <URL: http://www.ncbi.nlm.nih.gov/nuccore/AF338717>; 2 pgs.

National Center for Biotechnology Information, National Library of Medicine, National Institutes of Health, GenBank Locus AF419314, Accession No. AF419314, "Avian infectious bronchitis virus isolate PA/171/99 S1 surface glycoprotein (S1) gene, partial cds" [online]. Bethesda, MD [retrieved on Aug. 1, 2016]. Retrieved from the Internet: <URL: http://www.ncbi.nlm.nih.gov/nuccore/AF419314>; 2 pgs.

National Center for Biotechnology Information, National Library of Medicine, National Institutes of Health, GenBank Locus AF419315, Accession No. AF419315, "Avian infectious bronchitis virus isolate CA/Machado/88 S1 surface glycoprotein (S1) gene, partial cds" [online]. Bethesda, MD [retrieved on Aug. 4, 2016]. Retrieved from the Internet: <URL: http://www.ncbi.nlm.nih.gov/nuccore/AF419315>; 2 pgs.

National Center for Biotechnology Information, National Library of Medicine, National Institutes of Health, GenBank Locus AF510565, Accession No. AF510565, "Avian infectious bronchitis virus isolate AL/11274/97 S1 glycoprotein gene, partial cds" [online]. Bethesda, MD [retrieved on Aug. 4, 2016]. Retrieved from the Internet: <URL: http://www.ncbi.nlm.nih.gov/nuccore/AF510565>; 2 pgs.

(Continued)

*Primary Examiner* — Benjamin P Blumel
(74) *Attorney, Agent, or Firm* — Mueting, Raasch & Gebhardt, P.A.

(57) ABSTRACT

The present invention provides the isolation and characterization of a new infectious bronchitis virus (IBV) variant, the IBV GA-13 variant, and the production of attenuated isolates thereof, including, but not limited to, the attenuated IBV GA13 isolate 103505 Kd E86, and the use of such IBV isolates in materials and methods for combating infectious bronchitis virus in poultry and reducing the economic impact that infectious bronchitis disease has on poultry production.

19 Claims, 9 Drawing Sheets

(56) References Cited

OTHER PUBLICATIONS

Figure 2:
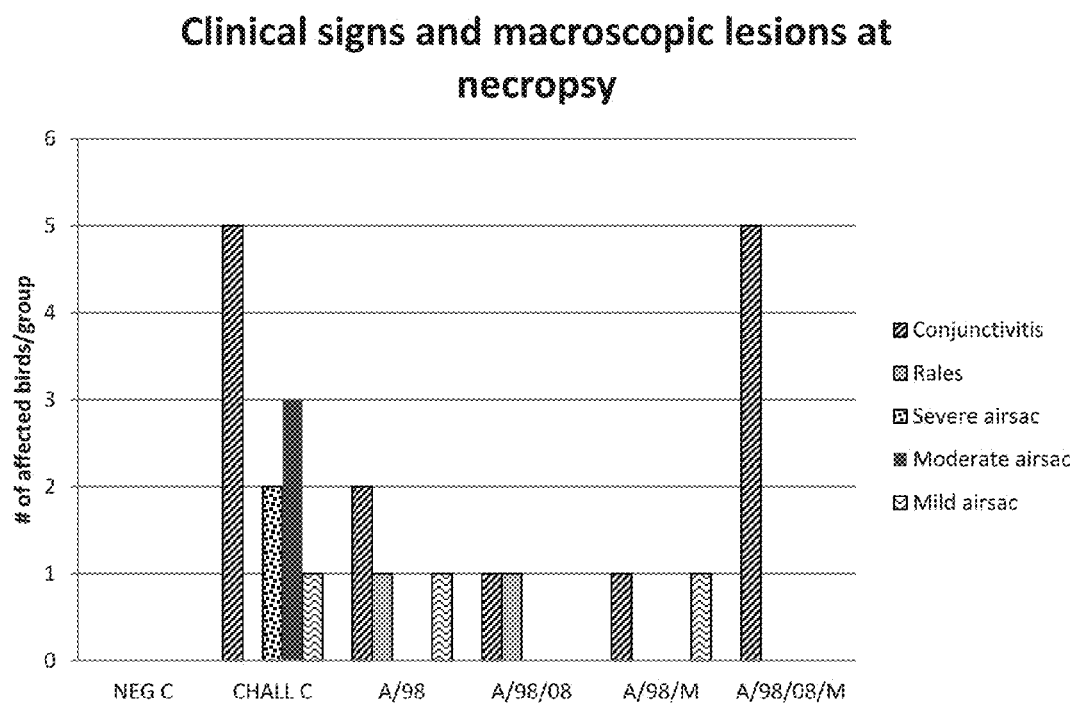

National Center for Biotechnology Information, National Library of Medicine, National Institutes of Health, GenBank Locus AF520607, Accession No. AF520607, "Avian infectious bronchitis virus IA/10624/99 S1 glycoprotein gene, partial cds" [online]. Bethesda, MD [retrieved on Aug. 4, 2016]. Retrieved from the Internet: <URL: http://www.ncbi.nlm.nih.gov/nuccore/AF520607>; 2 pgs.

National Center for Biotechnology Information, National Library of Medicine, National Institutes of Health, GenBank Locus AY789944, Accession No. AY789944, "Avian infectious bronchitis virus strain PA/4327/97 B S1 surface glycoprotein gene, partial cds" [online]. Bethesda, MD [retrieved on Aug. 4, 2016]. Retrieved from the Internet: <URL: http://www.ncbi.nlm.nih.gov/nuccore/AY789944>; 2 pgs.

National Center for Biotechnology Information, National Library of Medicine, National Institutes of Health, GenBank Locus AY789945, Accession No. AY789945, "Avian infectious bronchitis virus strain PA/5083/99 S1 surface glycoprotein gene, partial cds" [online]. Bethesda, MD [retrieved on Aug. 4, 2016]. Retrieved from the Internet: <URL: http://www.ncbi.nlm.nih.gov/nuccore/AY789945>; 2 pgs.

National Center for Biotechnology Information, National Library of Medicine, National Institutes of Health, GenBank Locus AY851295, Accession No. AY851295, "Avian infectious bronchitis virus strain Mass 41, complete genome" [online]. Bethesda, MD [retrieved on Aug. 4, 2016]. Retrieved from the Internet: <URL: http://www.ncbi.nlm.nih.gov/nuccore/AY851295>; 10 pgs.

National Center for Biotechnology Information, National Library of Medicine, National Institutes of Health, GenBank Locus DQ912832, Accession No. DQ912832, "Infectious bronchitis virus strain CAL99 isolated in 1995 spike (S1) gene, partial cds" [online]. Bethesda, MD [retrieved on Aug. 4, 2016]. Retrieved from the Internet: <URL: http://www.ncbi.nih.gov/nuccore/DQ912832>; 2 pgs.

National Center for Biotechnology Information, National Library of Medicine, National Institutes of Health, GenBank Locus EU283057, Accession No. EU283057, "Infectious bronchitis virus isolate Conn/Bvial1 S1 protein (S1) gene, partial cds" [online]. Bethesda, MD [retrieved on Aug. 4, 2016]. Retrieved from the Internet: <URL: http://www.ncbi.nlm.nih.gov/nuccore/EU283057>; 2 pgs.

National Center for Biotechnology Information, National Library of Medicine, National Institutes of Health, GenBank Locus EU283062, Accession No. EU283062, "Infectious bronchitis virus isolate Conn/Cvial2 S1 protein (S1) gene, partial cds" [online]. Bethesda, MD [retrieved on Aug. 4, 2016]. Retrieved from the Internet: <URL: http://www.ncbi.nlm.nih.gov/nuccore/EU283062>; 2 pgs.

National Center for Biotechnology Information, National Library of Medicine, National Institutes of Health, GenBank Locus EU359657, Accession No. EU359657, "Infectious bronchitis virus strain Mass commercial vaccine spike glycoprotein gene, partial cds" [online]. Bethesda, MD [retrieved on Aug. 4, 2016]. Retrieved from the Internet: <URL: http://www.ncbi.nlm.nih.gov/nuccore/EU359657>; 2 pgs.

National Center for Biotechnology Information, National Library of Medicine, National Institutes of Health, GenBank Locus GQ484958, Accession No. GQ484958, "Infectious bronchitis virus isolate ArkDPI_vaccine_B-6 spike glycoprotein gene, complete cds" [online]. Bethesda, MD [retrieved on Aug. 4, 2016]. Retrieved from the Internet: <URL: http://www.ncbi.nlm.nih.gov/nuccore/GQ484958>; 3 pgs.

National Center for Biotechnology Information, National Library of Medicine, National Institutes of Health, GenBank Locus GU301925, Accession No. GU301925, "Infectious bronchitis virus isolate Georgia 08 S1 protein (S1) gene, partial cds" [online]. Bethesda, MD [retrieved on Aug. 4, 2016]. Retrieved from the Internet: <URL: http://www.ncbi.nlm.nih.gov/nuccore/GU301925>; 2 pgs.

National Center for Biotechnology Information, National Library of Medicine, National Institutes of Health, GenBank Locus JN160805, Accession No. JN160805, "Infectious bronchitis virus isolate GA/60173/2007 S1 spike glycoprotein gene, partial cds" [online]. Bethesda, MD [retrieved on Aug. 4, 2016]. Retrieved from the Internet: <URL: http://www.ncbi.nlm.nih.gov/nuccore/JN160805>; 2 pgs.

National Center for Biotechnology Information, National Library of Medicine, National Institutes of Health, GenBank Locus JN192154, Accession No. JN192154, "Infectious bronchitis virus isolate 4/91(UK) spike glycoprotein (S) gene, partial cds" [online]. Bethesda, MD [retrieved on Aug. 4, 2016]. Retrieved from the Internet: <URL: http://www.ncbi.nlm.nih.gov/nuccore/JN192154>; 2 pgs.

National Center for Biotechnology Information, National Library of Medicine, National Institutes of Health, GenBank Locus JQ660957, Accession No. JQ660957, "Infectious bronchitis virus isolate ArkDPI vaccine B-19 spike glycoprotein gene, complete cds" [online]. Bethesda, MD [retrieved on Aug. 4, 2016]. Retrieved from the Internet: <URL: http://www.ncbi.nlm.nih.gov/nuccore/JQ660957>; 2 pgs.

Callison et al., "Development and evaluation of a real-time Taqman RT-PCR assay for the detection of infectious bronchitis virus from infected chickens" *J Virol Methods*, Dec. 2006; 138(1-2):60-65.

Callison et al. "Rapid differentiation of avian infectious bronchitis virus isolates by sample to residual ratio quantitation using real-time reverse transcriptase-polymerase chain reaction" *Journal of Virological Methods*, 2005; 124:183-90.

Candelora et al. "Survey for antibodies to infectious bursal disease virus serotype 2 in wild turkeys and Sandhill Cranes of Florida, USA" *J Wildl Dis*, Jul. 2010; 46(3):742-52.

Cavanagh et al., "Amino acids within hypervariable region 1 of avian coronavirus IBV (Massachusetts serotype) spike glycoprotein are associated with neutralization epitopes" *Virus Res*, Sep. 1988; 11(2):141-50.

Cavanagh et al., "Infectious bronchitis" in *Diseases of poultry, 11th ed*. Saif et al., Eds. Iowa State University Press: Ames, Iowa; 2003. Cover page, publisher's page, and pp. 101-119.

Cavanagh, "Severe acute respiratory syndrome vaccine development: experiences of vaccination against avian infectious bronchitis coronavirus" *Avian Pathol*, Dec. 2003; 32(6):567-82.

Cook et al., "Breadth of protection of the respiratory tract provided by different live-attenuated infectious bronchitis vaccines against challenge with infectious bronchitis viruses of heterologous serotypes" *Avian Pathol*, Oct. 1999; 28(5):477-85.

Dale et al., "Pathogenicity of a Novel Infectious Bronchitis Virus from Clinical Cases in the Southeastern United States" Presented at the AVMA/AAAP meeting, Denver Colorado, Jul. 27, 2014; 19 pages.

Durairaj et al. "An in vivo experimental model to determine antigenic variations among infections bursal disease viruses" *Avian Pathol*, Aug. 2013; 42(4):309-15.

Durairaj et al. "Investigation of the antigenic evolution of field isolates using the reverse genetics system of infections bursal disease virus (IBDV)" *Arch Virol*, Oct. 2011;156(10):1717-28.

Gelb et al., "Characterization of nephropathogenic infectious bronchitis virus DMV/1639/11 recovered from Delmarva broiler chickens in 2011" *Avian Dis*, Mar. 2013; 57(1):65-70.

Gelb et al., "Infectious Bronchitis Virus" in *A Laboratory Manual for the Isolation, Identification, and Characterization of Avian Pathogens, 5th Ed*. Dufour-Zavala et al., Eds. American Association of Avian Pathologists, Kennett Square, PA; 2008. Cover page, publisher's page, and pp. 146-149. 6 pages.

Icard et al. "Detection of infectious bursal disease virus isolates with unknown antigenic properties by reverse genetics" *Avian Dis*, Dec. 2008; 52(4):590-98.

Jackwood et al., Data from 11 years of molecular typing infectious bronchitis virus field isolates *Avian Dis*, Dec. 2005; 49(4):614-8.

(56) References Cited

OTHER PUBLICATIONS

Jackwood et al., "Molecular and Serologic Characterization, Pathogenicity, and Protection Studies with Infectious bronchitis virus field isolates from California" *Avian Dis.* Jun. 2007; 51(2):527-33.

Jackwood et al. "Rapid heat-treatment of attenuation of infectious bronchitis virus" *Avian Pathology*, Jun. 2010; 39(3):227-33.

Kapczynski et al. "Detection of in ovo-inoculated infectious bronchitis virus by immunohistochemistry and in situ hybridization with a riboprobe in epithelial cells of the lunch and cloacal bursa" *Avian Dis*, Jul.-Sep. 2002; 46(3):679-85.

Kapczynski et al. "Protection of chickens from infectious bronchitis by in ovo and intramuscular vaccination with a DNA vaccine expressing the S1 glycoprotein" *Avian Dis*, Apr.-Jun. 2003; 47(2):272-85.

King et al., "Evaluation of the hemagglutination-inhibition test for measuring the response of chickens to avian infectious bronchitis virus vaccination" *Avian Dis*, Jan.-Mar. 1983; 27(1):100-12.

Koch et al., "Antigenic domains on the peplomer protein of avian infectious bronchitis virus: correlation with biological functions" *J Gen Virol*, Sep. 1990; 71(Pt 9): 1929-35.

Kwon et al., "Differentiation of infectious bronchitis virus serotypes using polymerase chain reaction and restriction fragment length polymorphism analysis" *Avian Dis*, Jan.-Mar. 1993; 37(1):194-202.

Lashgari et al., "Serological comparison and antigenic relationships of seven serotypes of infectious bronchitis virus using the hemagglutination-inhibition test" *Avian Dis*, Apr.-Jun. 1984; 28(2):435-43.

Lee et al., "Evidence of genetic diversity generated by recombination among avian coronavirus IBV" *Arch Virol*, 2000; 145(10):2135-48.

Lee et al., "Redesign of primer and application of the reverse transcriptase-polymerase chain reaction and restriction fragment length polymorphism test to the DE072 strain of infectious bronchitis virus" *Avian Dis*, Jul.-Sep. 2000; 44(3):650-4.

Lee et al., "Origin and evolution of Georgia 98 (GA98), a new serotype of avian infectious bronchitis virus" *Virus Res*, Nov. 28, 2001; 80(1-2)33-9.

Lee et al., "Typing of field isolates of infectious bronchitis virus based on the sequence of the hypervariable region in the S1 gene" *J Vet Diagn Invest*, 2003; 15:344-8.

Lohr, "Infectious bronchitis agar-gel precipitin test—use of infected allantoic fluid as antigen" *Avian Dis*, Apr.-Jun, 1980; 24(2):463-7.

Lohr, "Diagnosis of infectious bronchitis (IB) by examination of tracheal mucus for IB-precipitating antigens" *Avian Dis*, Oct.-Dec. 1981; 25(4):1058-64.

Malinak et al., "Tribasic Copper Chloride Toxicosis in Commercial Brioler Chicks" *Avian Diseases*, Jul. 2014; 58(4):642-9.

Masters, "The molecular biology of coronaviruses" *Adv Vir Res*, 2006; 66:193-292.

Moore et al., "Identification of amino acids involved in a serotype and neutralization specific epitope within the s1 subunit of avian infectious bronchitis virus" *Arch Virol*, 1997; 142(11):2249-56.

Petkov et al. "Full-length sequence analysis of four IBDV strains with different pathogenicities" *Virus Genes*, Jun. 2007; 34(3):315-26.

Petkov et al. "Identification and characterization of two distinct bursal B-cell subpopulations following infectious bursal disease virus infection of White Leghorn chickens" *Avian Dis*, Sep. 2009; 53(3):347-55.

Ruano et al., "A rapid-plate hemagglutination assay for the detection of infectious bronchitis virus" *Avian Dis*, Jan.-Mar. 2000; 44(1):99-104.

Sellers et al. "Antigenic and molecular characterization of three infectious bursal disease virus field isolates" *Avian Dis*, Apr.-Jun. 1999; 43(2):198-206.

Sellers et al. "Detection of infectious bursal disease virus in experimentally infected chickens by in situ hybridization" *Avian Dis*, Jan.-Mar. 2001; 45(1):26-33.

Sellers et al. "Pathogenicity of a Novel Infectious Bronchitis Virus from Clinical Cases in North Georgia," AAAP Symposium & Scientific Program. Infection Bronchitis Virus, Denver, Colorado, Jul. 27, 2014.

Sellers et al. "Recent Isolation and Characterization of Nephrotropic and Variant Infectious bronchitis Virus Isolates from Georgia" *The Poultry Informed Professional*, Mar./Apr. 2008; (98):1-7.

Tatusova et al, "BLAST 2 Sequences, a new tool for comparing protein and nucleotide sequences," *FEMS Microbiol Lett*, 1999; 174:247-250.

Toro et al., "Transfer of IgG from serum to lachrymal fluid in chickens" *Avian Dis*, Jan.-Mar. 1993; 37(1):60-6.

Villegas, "Titration of biological suspensions" in *A Laboratory Manual for the Isolation, Identification, and Characterization of Avian Pathogens*, 5th ed. Dufour-Zavala et al., Eds. American Association of Avian Pathologists, Kennett Square, PA; 2008. Cover page, publisher's page, and pp. 217-21. 7 pages.

Figure 1

Figure 6

```
                              10         20         30         40         50         60         70         80
                     ----------+---------+---------+---------+---------+---------+---------+---------+
103505 Kd E3 IBVS1S1.seq      ATGTCGGTAATACCTCTTTTGCTAGTGAGTGACTCTTTTGTTTGCACTATGTGCTTTGCTGTGCTGCTTTGTATGATAATGATTCTTTCGT   80
103505kdE86 MSV IBVS1.seq     ............................................................................   80
                     ----------+---------+---------+---------+---------+---------+---------+---------+
                              10         20         30         40         50         60         70         80

90        100        110        120        130        140        150        160
                     ----------+---------+---------+---------+---------+---------+---------+---------+
103505 Kd E3 IBVS1S1.seq      TTACTACTACCAAAGTGCCTTCAGACCATATGATGGCTGGCATTTACATGGAGGTGCTTATGAAGTTATTAATACTACTC   160
103505kdE86 MSV IBVS1.seq     ...........................................................C..............   160
                     ----------+---------+---------+---------+---------+---------+---------+---------+
                              90        100        110        120        130        140        150        160

170        180        190        200        210        220        230        240
                     ----------+---------+---------+---------+---------+---------+---------+---------+
103505 Kd E3 IBVS1S1.seq      AGGAAATTTAATAATGCAGGTTTAAATTCTGAATGTACTGCTGGTGCCATTTCTTGGAGTAAGAATTTTCTGCTGCTTCT   240
103505kdE86 MSV IBVS1.seq     .........................T..................................................   240
                     ----------+---------+---------+---------+---------+---------+---------+---------+
                              170        180        190        200        210        220        230        240

250        260        270        280        290        300        310        320
                     ----------+---------+---------+---------+---------+---------+---------+---------+
103505 Kd E3 IBVS1S1.seq      GTAGCCATGACTGCACCATATAATGTATGTCGTGTCTGTTCAGCAATTTTGCACGGCGCACTGTAATTTTACTTATTT   320
103505kdE86 MSV IBVS1.seq     ..............................................................................   320
                     ----------+---------+---------+---------+---------+---------+---------+---------+
                              250        260        270        280        290        300        310        320

330        340        350        360        370        380        390        400
                     ----------+---------+---------+---------+---------+---------+---------+---------+
103505 Kd E3 IBVS1S1.seq      TACAGTGTTTGTTACACATTGTTTATAAGGCGGAGTTGGCACGTGTCCTTTAACAGGTATGATTCCACAAAACCAAATCC   400
103505kdE86 MSV IBVS1.seq     ........................................................T.....................   400
                     ----------+---------+---------+---------+---------+---------+---------+---------+
                              330        340        350        360        370        380        390        400

410        420        430        440        450        460        470        480
                     ----------+---------+---------+---------+---------+---------+---------+---------+
103505 Kd E3 IBVS1S1.seq      GCATTTCTGCTATGAGAAGCGGTAGTGCTCCCCCGGATCTTTTTTACAATTTAACAGTTCCTGTGACTAAATATCCTTCA   480
103505kdE86 MSV IBVS1.seq     ..............................................................................   480
                     ----------+---------+---------+---------+---------+---------+---------+---------+
                              410        420        430        440        450        460        470        480

490        500        510        520        530        540        550        560
                     ----------+---------+---------+---------+---------+---------+---------+---------+
103505 Kd E3 IBVS1S1.seq      TTTAAGTCACTCCAATGTGTTCATTTTAAAGCTGGTGGACCATCAAACGTCTGTATATTTAAATGGTGATCTTGTTTTTCATCTAATGAGACTAT   560
103505kdE86 MSV IBVS1.seq     ..............................................................................   560
                     ----------+---------+---------+---------+---------+---------+---------+---------+
                              490        500        510        520        530        540        550        560

570        580        590        600        610        620        630        640
                     ----------+---------+---------+---------+---------+---------+---------+---------+
103505 Kd E3 IBVS1S1.seq      AGATGTTTCAGGTGCAGGTGTTCATTTTAAAGCTGGTGGACCATTAACCTATAAAGTTATGAGAGAAGTTAAAGCCCTGG   640
103505kdE86 MSV IBVS1.seq     ..G...........................................................................   640
                     ----------+---------+---------+---------+---------+---------+---------+---------+
                              570        580        590        600        610        620        630        640
```

Figure 6 (continued)

```
                        1290      1300      1310      1320      1330      1340      1350      1360
                       ----+----|----+----|----+----|----+----|----+----|----+----|----+----|----+----|
103505_Kd_E3_IBVS1s1.seq  AAATTTTATATAATAACATCACTTAGATAGGTGTGTTGATTATAACATATGGCAGAGTAGGCCAAGGTTTATAACTA   1360
103505kdE86_MSV_IBVS1.seq ............................................................................   1360

1370      1380      1390      1400      1410      1420      1430      1440
                       ----+----|----+----|----+----|----+----|----+----|----+----|----+----|----+----|
103505_Kd_E3_IBVS1s1.seq  ATGTAACTGACTCAACTGCTGATTATAATTATTTAGCAGATGGAGGGTTAGCTATTTTAGACACATCAGGTGCTATAGAC   1440
103505kdE86_MSV_IBVS1.seq ............................................................................   1440

1450      1460      1470      1480      1490      1500      1510      1520
                       ----+----|----+----|----+----|----+----|----+----|----+----|----+----|----+----|
103505_Kd_E3_IBVS1s1.seq  ATCTTCGTTGTACAAGGTGAATATGGCCTTAATTTTTATAAGGTTAATCCTTGCGAAGATGTTAATCAGCAGTTTGTAGT   1520
103505kdE86_MSV_IBVS1.seq ............................................................................   1520

1530      1540      1550      1560      1570      1580      1590      1600
                       ----+----|----+----|----+----|----+----|----+----|----+----|----+----|----+----|
103505_Kd_E3_IBVS1s1.seq  TTCTGGTGGTAAGTTAGTAGGTGTTCTTACTTCACGTAATGAAACTGATTCTCAGTTTCTTGAGAACCAGTTTACATTA   1600
103505kdE86_MSV_IBVS1.seq ............................................................................   1600

1610
                       ----+----|
103505_Kd_E3_IBVS1s1.seq  AACTCACTAATGAA   1614
103505kdE86_MSV_IBVS1.seq .........A..   1614
```

Figure 8

Tracheal lesion scores for GA13 E86 MSV

Figure 9

Mean Tracheal Lesion Scores
scale 1-4

SEQUENCE LISTING

```
<160> NUMBER OF SEQ ID NOS: 6

<210> SEQ ID NO 1
<211> LENGTH: 1622
<212> TYPE: DNA
<213> ORGANISM: Infectious bronchitis virus

<400> SEQUENCE: 1
atgtcggtaa tacctctttt gctagtgact cttttgtttg cactatgtag tgctgctttg        60
tatgataatg attctttcgt ttactactac caaagtgcct tcagaccata tgatggctgg       120
catttacatg gaggtgctta tgaagttatt aatactactc aggaatttaa taatgcaggt       180
ttaaattctg aatgtactgc tggtgccatt tcttggagta agaattttc tgctgcttct        240 gtagccatga ctgcaccata taatggtatg tcgtggtctg ttcagcaatt ttgcacggcg       300
cactgtaatt ttacttattt tacagtgttt gttacacatt gttataagcg cggagttggc       360
acgtgtcctt taacaggtat gattccacaa aaccaaatcc gcatttctgc tatgagaagc       420
ggtagtgctc ccccggatct ttttacaat ttaacagttc ctgtgactaa atatccttca        480
tttaagtcac tccaatgtgt taataatcaa acgtctgtat atttaaatgg tgatcttgtt       540
ttttcatcta atgagactat agatgtttca ggtgcaggtg ttcatttaa agctggtgga       600 cccataacct ataaagttat gagagaagtt aaagccctgg cttatttgt taatggtacc        660 gcacaagatg tcatttttgtg cgatggtaca cccagaggtt tgttagcatg ccaatataat       720
actggcaatt ttacagatgg cttctatcct tttactaata gtagtttagt taaggaaaag       780
```

```
tttattgtct atcgtgagaa tagtgttaac gccactttgg ttttacataa tattacgttt      840
tttaatgaga ctagtgcacc acctgccggc ggtgatatta gtgctatatt tccaacttat      900
caaatggtaa cagctcagag tggttattat aatttaatt tctcatttct gagtggtttt       960
gtttataagg taagtgattt tatgtatggg tcttaccacc caaagtgtaa ttttagacca     1020
gaaaatctta ataatgacct ctggtttaat tcactctcaa tctcacttgc ttatggccca     1080
ctacaagggg gctgtaagca gtcggttttt aatggtagag caacgtgttg ttatgcttat     1140
tcatacaacg gtcctcatgc ttgtaaaggt gtctatcgag gtcagttaca acaatatttt     1200
gaatgtgggt tgctagttta tattactaag agcgatggct ctcgtataca aacagcaaca     1260
aaagcacctg tagtaactac aaattttat aataacatca ctttagatag gtgtgttgat     1320
tataacatat atggcagagt aggccaaggt tttataacta atgtaactga ctcaactgct     1380
gattataatt atttagcaga tggagggtta gctatttag acacatcagg tgctatagac     1440
atcttcgttg tacaaggtga atatggcctt aattttata aggttaatcc ttgcgaagat     1500
gttaatcagc agtttgtagt ttctggtggt aagttagtag gtgttcttac ttcacgtaat     1560
gaaactgatt ctcagtttct tgagaaccag ttttacatta aactcactaa tgaaacacat     1620
cg                                                                     1622
```

<210> SEQ ID NO 2
<211> LENGTH: 540
<212> TYPE: PRT
<213> ORGANISM: Infectious bronchitis virus

<400> SEQUENCE: 2

```
Met Ser Val Ile Pro Leu Leu Val Thr Leu Leu Phe Ala Leu Cys
1               5                   10                  15

Ser Ala Ala Leu Tyr Asp Asn Asp Ser Phe Val Tyr Tyr Gln Ser
                20                  25                  30

Ala Phe Arg Pro Tyr Asp Gly Trp His Leu His Gly Gly Ala Tyr Glu
            35                  40                  45

Val Ile Asn Thr Thr Gln Glu Phe Asn Asn Ala Gly Leu Asn Ser Glu
        50                  55                  60

Cys Thr Ala Gly Ala Ile Ser Trp Ser Lys Asn Phe Ser Ala Ala Ser
65                  70                  75                  80

Val Ala Met Thr Ala Pro Tyr Asn Gly Met Ser Trp Ser Val Gln Gln
                85                  90                  95

Phe Cys Thr Ala His Cys Asn Phe Thr Tyr Phe Thr Val Phe Val Thr
            100                 105                 110

His Cys Tyr Lys Arg Gly Val Gly Thr Cys Pro Leu Thr Gly Met Ile
        115                 120                 125

Pro Gln Asn Gln Ile Arg Ile Ser Ala Met Arg Ser Gly Ser Ala Pro
    130                 135                 140

Pro Asp Leu Phe Tyr Asn Leu Thr Val Pro Val Thr Lys Tyr Pro Ser
145                 150                 155                 160

Phe Lys Ser Leu Gln Cys Val Asn Asn Gln Thr Ser Val Tyr Leu Asn
                165                 170                 175

Gly Asp Leu Val Phe Ser Ser Asn Glu Thr Ile Asp Val Ser Gly Ala
            180                 185                 190

Gly Val His Phe Lys Ala Gly Gly Pro Ile Thr Tyr Lys Val Met Arg
        195                 200                 205

Glu Val Lys Ala Leu Ala Tyr Phe Val Asn Gly Thr Ala Gln Asp Val
```

```
        210                 215                 220
Ile Leu Cys Asp Gly Thr Pro Arg Gly Leu Leu Ala Cys Gln Tyr Asn
225                 230                 235                 240

Thr Gly Asn Phe Thr Asp Gly Phe Tyr Pro Phe Thr Asn Ser Ser Leu
                245                 250                 255

Val Lys Glu Lys Phe Ile Val Tyr Arg Glu Asn Ser Val Asn Ala Thr
                260                 265                 270

Leu Val Leu His Asn Ile Thr Phe Phe Asn Glu Thr Ser Ala Pro Pro
            275                 280                 285

Ala Gly Gly Asp Ile Ser Ala Ile Phe Pro Thr Tyr Gln Met Val Thr
        290                 295                 300

Ala Gln Ser Gly Tyr Tyr Asn Phe Asn Phe Ser Phe Leu Ser Gly Phe
305                 310                 315                 320

Val Tyr Lys Val Ser Asp Phe Met Tyr Gly Ser Tyr His Pro Lys Cys
                325                 330                 335

Asn Phe Arg Pro Glu Asn Leu Asn Asn Asp Leu Trp Phe Asn Ser Leu
                340                 345                 350

Ser Ile Ser Leu Ala Tyr Gly Pro Leu Gln Gly Gly Cys Lys Gln Ser
            355                 360                 365

Val Phe Asn Gly Arg Ala Thr Cys Cys Tyr Ala Tyr Ser Tyr Asn Gly
        370                 375                 380

Pro His Ala Cys Lys Gly Val Tyr Arg Gly Gln Leu Gln Gln Tyr Phe
385                 390                 395                 400

Glu Cys Gly Leu Leu Val Tyr Ile Thr Lys Ser Asp Gly Ser Arg Ile
                405                 410                 415

Gln Thr Ala Thr Lys Ala Pro Val Val Thr Thr Asn Phe Tyr Asn Asn
                420                 425                 430

Ile Thr Leu Asp Arg Cys Val Asp Tyr Asn Ile Tyr Gly Arg Val Gly
            435                 440                 445

Gln Gly Phe Ile Thr Asn Val Thr Asp Ser Thr Ala Asp Tyr Asn Tyr
        450                 455                 460

Leu Ala Asp Gly Gly Leu Ala Ile Leu Asp Thr Ser Gly Ala Ile Asp
465                 470                 475                 480

Ile Phe Val Val Gln Gly Glu Tyr Gly Leu Asn Phe Tyr Lys Val Asn
                485                 490                 495

Pro Cys Glu Asp Val Asn Gln Gln Phe Val Val Ser Gly Gly Lys Leu
                500                 505                 510

Val Gly Val Leu Thr Ser Arg Asn Glu Thr Asp Ser Gln Phe Leu Glu
            515                 520                 525

Asn Gln Phe Tyr Ile Lys Leu Thr Asn Glu Thr His
        530                 535                 540

<210> SEQ ID NO 3
<211> LENGTH: 1614
<212> TYPE: DNA
<213> ORGANISM: Artificial Sequence
<220> FEATURE:
<223> OTHER INFORMATION: Description of Artificial Sequence: Synthetic
      polynucleotide

<400> SEQUENCE: 3
atgtcggtaa taccttcttt gctagtgact cttttgtttg cactatgtag tgctgctttg      60
tatgataatg attctttcgt ttactactac caaagtgcct tcagaccata tgatggctgg     120
catttacatg gaggtgctta tcaagttatt aatactactc aggaatttaa taatgcaggt     180
```

```
ttaaattctg aatgtactgc tggtgtcatt tcttggagta agaatttttc tgctgcttct    240
gtagccatga ctgcaccata taatggtatg tcgtggtctg ttcagcaatt ttgcacggcg    300
cactgtaatt ttacttattt tacagtgttt gttacacatt gttataagcg cggagttggc    360
atgtgtcctt taacaggtat gattccacaa aaccaaatcc gcatttctgc tatgagaagc    420
ggtagtgctc ccccggatct ttttttacaat ttaacagttc ctgtgactaa atatccttca    480
tttaagtcac tccaatgtgt taataatcaa acgtctgtat atttaaatgg tgatcttgtt    540
ttttcatcta atgagactat aggtgtttca ggtgcaggtg ttcattttaa agctggtgga    600
cccataacct ataaagttat gagagaagtt aaagccctgg cttatttttgt taatggtacc    660
gcacaagatg tcattttgtg cgatggtaca cccagaggtt tgttagcatg ccaatataat    720
actggcaatt ttacagatgg cttctatcct tttactaata gtagtttagt taaggaaaag    780
tttattgtct atcgtgagaa tagtgttaac gccacttttgg ttttacataa tattacgttt    840
tttaatgaga ctagtgcacc acctgccggc ggtgatatta gtgctatatt tccaacttat    900
caaatggtaa cagctcagag tggttattat aattttaatt tctcatttct gagtggtttt    960
gtttataagg tacgtgattt tatgtatggg tcttaccacc caaagtgtaa ttttagacca   1020
gaaaatctta ataatgacct ctggtttaat tcactctcaa tctcacttgc ttatggccca   1080
ctacaagggg gctgtaagca gtcggttttt aatggtagag caacgtgttg ttatgcttat   1140
tcatacaacg tcctcatgc ttgtaaaggt gtctatcgag gtcagttaca acaatatttt   1200
gaatgtgggt tgctagttta tattactaag agcgatggct ctcgtataca aacagcaaca   1260
aaaagcacctg tagtaactac aaattttttat aataacatca ctttagatag gtgtgttgat   1320
tataacatat atggcagagt aggccaaggt tttataacta atgtaactga ctcaactgct   1380
gattataatt attagcaga tggagggtta gctatttttag acacatcagg tgctatagac   1440
atcttcgttg tacaaggtga atatggcctt aattttttata aggttaatcc ttgcgaagat   1500
gttaatcagc agtttgtagt ttctggtggt aagttagtag gtgttcttac ttcacgtaat   1560
gaaactgatt ctcagtttct tgagaaccag ttttacatta aactcactaa taaa         1614
```

<210> SEQ ID NO 4
<211> LENGTH: 538
<212> TYPE: PRT
<213> ORGANISM: Artificial Sequence
<220> FEATURE:
<223> OTHER INFORMATION: Description of Artificial Sequence: Synthetic
    polypeptide

<400> SEQUENCE: 4

Met Ser Val Ile Pro Leu Leu Val Thr Leu Leu Phe Ala Leu Cys
1               5                   10                  15

Ser Ala Ala Leu Tyr Asp Asn Asp Ser Phe Val Tyr Tyr Gln Ser
                20                  25                  30

Ala Phe Arg Pro Tyr Asp Gly Trp His Leu His Gly Ala Tyr Gln
            35                  40                  45

Val Ile Asn Thr Thr Gln Glu Phe Asn Asn Ala Gly Leu Asn Ser Glu
        50                  55                  60

Cys Thr Ala Gly Val Ile Ser Trp Ser Lys Asn Phe Ser Ala Ser
65                  70                  75                  80

Val Ala Met Thr Ala Pro Tyr Asn Gly Met Ser Trp Ser Val Gln Gln
                85                  90                  95

Phe Cys Thr Ala His Cys Asn Phe Thr Tyr Phe Thr Val Phe Val Thr
            100                 105                 110

-continued

```
His Cys Tyr Lys Arg Gly Val Gly Met Cys Pro Leu Thr Gly Met Ile
            115                 120                 125

Pro Gln Asn Gln Ile Arg Ile Ser Ala Met Arg Ser Gly Ser Ala Pro
        130                 135                 140

Pro Asp Leu Phe Tyr Asn Leu Thr Val Pro Val Thr Lys Tyr Pro Ser
145                 150                 155                 160

Phe Lys Ser Leu Gln Cys Val Asn Asn Gln Thr Ser Val Tyr Leu Asn
                165                 170                 175

Gly Asp Leu Val Phe Ser Ser Asn Glu Thr Ile Gly Val Ser Gly Ala
            180                 185                 190

Gly Val His Phe Lys Ala Gly Pro Ile Thr Tyr Lys Val Met Arg
        195                 200                 205

Glu Val Lys Ala Leu Ala Tyr Phe Val Asn Gly Thr Ala Gln Asp Val
        210                 215                 220

Ile Leu Cys Asp Gly Thr Pro Arg Gly Leu Leu Ala Cys Gln Tyr Asn
225                 230                 235                 240

Thr Gly Asn Phe Thr Asp Gly Phe Tyr Pro Phe Thr Asn Ser Ser Leu
                245                 250                 255

Val Lys Glu Lys Phe Ile Val Tyr Arg Glu Asn Ser Val Asn Ala Thr
            260                 265                 270

Leu Val Leu His Asn Ile Thr Phe Phe Asn Glu Thr Ser Ala Pro Pro
        275                 280                 285

Ala Gly Gly Asp Ile Ser Ala Ile Phe Pro Thr Tyr Gln Met Val Thr
        290                 295                 300

Ala Gln Ser Gly Tyr Tyr Asn Phe Asn Phe Ser Phe Leu Ser Gly Phe
305                 310                 315                 320

Val Tyr Lys Val Arg Asp Phe Met Tyr Gly Ser Tyr His Pro Lys Cys
                325                 330                 335

Asn Phe Arg Pro Glu Asn Leu Asn Asn Asp Leu Trp Phe Asn Ser Leu
            340                 345                 350

Ser Ile Ser Leu Ala Tyr Gly Pro Leu Gln Gly Gly Cys Lys Gln Ser
        355                 360                 365

Val Phe Asn Gly Arg Ala Thr Cys Cys Tyr Ala Tyr Ser Tyr Asn Gly
        370                 375                 380

Pro His Ala Cys Lys Gly Val Tyr Arg Gly Gln Leu Gln Gln Tyr Phe
385                 390                 395                 400

Glu Cys Gly Leu Leu Val Tyr Ile Thr Lys Ser Asp Gly Ser Arg Ile
                405                 410                 415

Gln Thr Ala Thr Lys Ala Pro Val Val Thr Thr Asn Phe Tyr Asn Asn
            420                 425                 430

Ile Thr Leu Asp Arg Cys Val Asp Tyr Asn Ile Tyr Gly Arg Val Gly
        435                 440                 445

Gln Gly Phe Ile Thr Asn Val Thr Asp Ser Thr Ala Asp Tyr Asn Tyr
        450                 455                 460

Leu Ala Asp Gly Gly Leu Ala Ile Leu Asp Thr Ser Gly Ala Ile Asp
465                 470                 475                 480

Ile Phe Val Val Gln Gly Glu Tyr Gly Leu Asn Phe Tyr Lys Val Asn
                485                 490                 495

Pro Cys Glu Asp Val Asn Gln Gln Phe Val Val Ser Gly Gly Lys Leu
            500                 505                 510

Val Gly Val Leu Thr Ser Arg Asn Glu Thr Asp Ser Gln Phe Leu Glu
        515                 520                 525
```

```
Asn Gln Phe Tyr Ile Lys Leu Thr Asn Lys
    530                 535

<210> SEQ ID NO 5
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 5
gtttcaggyg caggtgttca                                                 20

<210> SEQ ID NO 6
<211> LENGTH: 20
<212> TYPE: DNA
<213> ORGANISM: Artificial Sequence
<220> FEATURE:
<223> OTHER INFORMATION: Description of Artificial Sequence: Synthetic
      primer

<400> SEQUENCE: 6
accactctga gctgttacca                                                 20
```

ATTENUATION OF INFECTIOUS BRONCHITIS VIRUS VARIANT GA-13

CONTINUING APPLICATION DATA

This application claims the benefit of U.S. Provisional Application Ser. No. 62/028,435, filed Jul. 24, 2014, which is incorporated by reference herein in its entirety.

SEQUENCE LISTING

The instant application contains a Sequence Listing which has been submitted electronically in ASCII format and is hereby incorporated by reference in its entirety. Said ASCII copy, created on Sep. 18, 2015, is named 235.02500101_SL.txt and is 14,658 bytes in size.

BACKGROUND

Infectious bronchitis virus (IBV) is a group 3 avian coronavirus that causes a highly contagious upper-respiratory tract disease in chickens characterized by tracheal rales, coughing, and sneezing. In addition, the disease may affect the kidneys, and in laying flocks there is usually a drop in egg production and egg quality. Mortality may occur in young chicks due to respiratory or kidney manifestations of the infection. The disease is prevalent worldwide with significant economic consequences.

Control of the disease is extremely important because IBV predisposes birds to potentially lethal secondary pathogens. Attenuated live vaccines and killed vaccines are used in an attempt to prevent the disease. However, extensive genetic diversity and a high mutation rate results in many different types of the virus that do not serologically cross-react, making it important to vaccinate chickens with the type of IBV causing the disease. IBV variant viruses are consistently circulating in commercial poultry and are capable of causing disease outbreaks. There is little cross-protection between different serotypes of IBV.

Control of IBV relies primarily on the use of mass applied modified live vaccines. Poultry producers face several challenges when trying to control IBV infections in the field. First, very little to no cross-protection is afforded between serotypes of IBV. Therefore, successful vaccination programs must include the serotypes of the prevailing IBV field challenge. Second, IBVs are prone to genetic variation through several distinct genetic mechanisms that may or may not give rise to a new serotype. A few changes in the sequence of the spike glycoprotein can result in a new serotype. It has been documented that as little as a 5% difference in the S1 sequence of IBV can result in a loss of cross-protection between otherwise similar isolates (Cavanagh, 2003, *Avian Pathol;* 32:567-582).

Identifying the type of IBV causing disease in commercial chickens is the first step in controlling this highly infectious virus, but it is of little value if commercially available vaccines do not protect against it. Thus there is a need for the characterization of newly arising IBV variant and the development of vaccines effective against these variants.

SUMMARY OF THE INVENTION

The present invention includes an attenuated infectious bronchitis virus (IBV) GA13 isolate, wherein the attenuated IBV GA13 isolate includes an attenuated isolate of GA13 PDRC accession number 103505.

In some aspects, an attenuated IBV GA13 isolate of the present invention includes a S1 glycoprotein subunit with at least one amino acid difference from the S1 glycoprotein subunit of IBV GA13 isolate GA13 PDRC accession number 103505.

In some aspects, an attenuated IBV GA13 IBV isolate of the present invention includes an attenuated isolate of GA13 PDRC accession number 103505 Kd E3.

In some aspects, the present invention includes an attenuated IBV GA13 having been attenuated by passage through embryonated eggs. In some aspects, attenuation includes any number of passages from 1 to 150 (EN, wherein N is an integer from 1 to 150). In some aspects, attenuation includes at least about 86 passages.

In some aspects, an attenuated IBV GA13 isolate of the present invention includes the IBV GA13 isolate 103505 KdE86.

In some aspects, the present invention includes an attenuated IBV GA13 isolate having an S1 glycoprotein subunit comprising an amino acid sequence comprising at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO:2 and/or SEQ ID NO:4.

In some aspects, the present invention includes an attenuated IBV GA13 isolate having a S1 glycoprotein subunit comprising any one, any two, any three, any four, or all five of the following amino acids residues: a glutamine at position 48; a valine at position 69; a methionine at position 121; a glycine at position 188; and/or an arginine at position 325.

In some aspects, the present invention includes an attenuated IBV GA13 isolate having a S1 glycoprotein subunit having at least one nucleotide sequence alteration and/or at least one amino acid alteration in comparison to a naturally occurring IBV isolate.

In some aspects, the present invention includes an attenuated IBV GA13 isolate having a S1 glycoprotein subunit encoded by a nucleotide sequence having at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO:1 and/or SEQ ID NO:3.

In some aspects, an attenuated IBV GA13 isolate of the present invention is lyophilized.

In some aspects, the present invention includes a composition including an attenuated IBV GA13 isolate of the present invention. In some aspects, a composition further includes other viral material.

In some aspects, the present invention includes a method including introducing an attenuated IBV GA13 isolate of the present invention, or a composition thereof, into the body of poultry. In some aspects, administration includes spraying.

In some aspects, the present invention includes a method of producing an immune response to the IBV virus in poultry, the method including administering an attenuated IBV GA13 isolate of the present invention, or a composition thereof, to poultry. In some aspects, administration includes spraying.

In some aspects, the present invention includes a method of preventing an IBV infection in poultry, the method including administering an attenuated IBV GA13 isolate of the present invention, or a composition thereof, to poultry. In some aspects, administration includes spraying.

Figure 5:
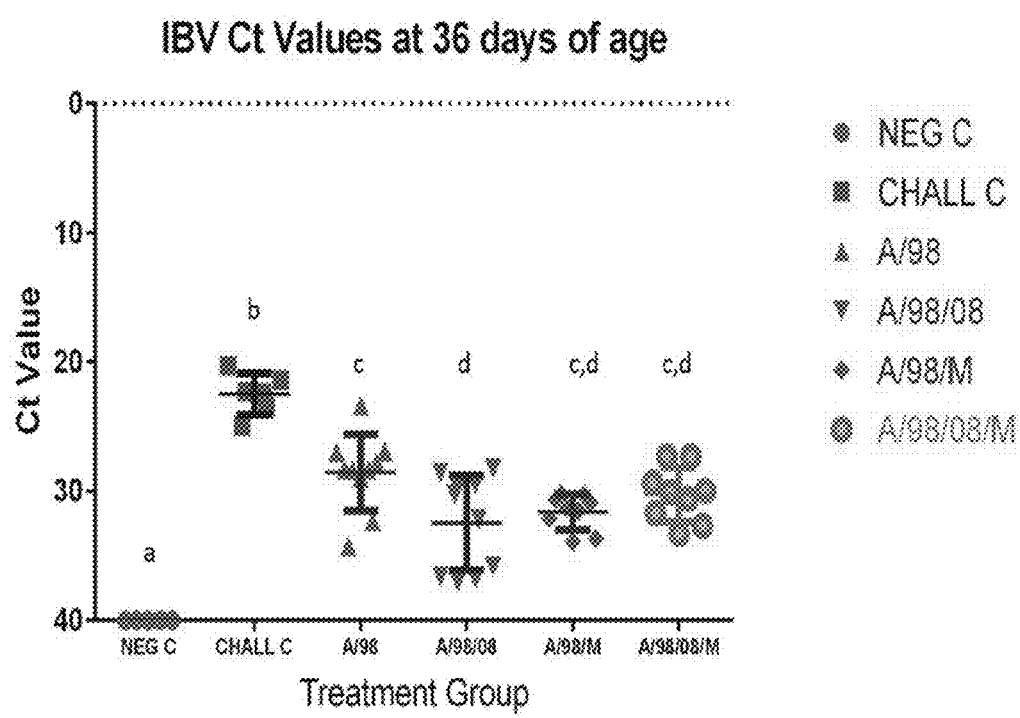

The present invention includes an isolated polynucleotide sequence with at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO:1 and/or SEQ ID NO:3. In some aspects, the present invention includes a vector including such an isolated nucleotide sequence.

The present invention includes an isolated polypeptide with at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, at least about 99% sequence identity, or 100% sequence identity to SEQ ID NO:2 and/or SEQ ID NO:4.

The terms "comprises" and variations thereof do not have a limiting meaning where these terms appear in the description and claims.

Unless otherwise specified, "a," "an," "the," and "at least one" are used interchangeably and mean one or more than one.

The term "and/or" means one or all of the listed elements or a combination of any two or more of the listed elements.

The words "preferred" and "preferably" refer to embodiments of the invention that may afford certain benefits, under certain circumstances. However, other embodiments may also be preferred, under the same or other circumstances. Furthermore, the recitation of one or more preferred embodiments does not imply that other embodiments are not useful, and is not intended to exclude other embodiments from the scope of the invention.

Also herein, the recitations of numerical ranges by endpoints include all numbers subsumed within that range (e.g., 1 to 5 includes 1, 1.5, 2, 2.75, 3, 3.80, 4, 5, etc.).

For any method disclosed herein that includes discrete steps, the steps may be conducted in any feasible order. And, as appropriate, any combination of two or more steps may be conducted simultaneously.

The above summary of the present invention is not intended to describe each disclosed embodiment or every implementation of the present invention. The description that follows more particularly exemplifies illustrative embodiments. In several places throughout the application, guidance is provided through lists of examples, which examples can be used in various combinations. In each instance, the recited list serves only as a representative group and should not be interpreted as an exclusive list.

Unless otherwise indicated, all numbers expressing quantities of components, molecular weights, and so forth used in the specification and claims are to be understood as being modified in all instances by the term "about." Accordingly, unless otherwise indicated to the contrary, the numerical parameters set forth in the specification and claims are approximations that may vary depending upon the desired properties sought to be obtained by the present invention. At the very least, and not as an attempt to limit the doctrine of equivalents to the scope of the claims, each numerical parameter should at least be construed in light of the number of reported significant digits and by applying ordinary rounding techniques.

Notwithstanding that the numerical ranges and parameters setting forth the broad scope of the invention are approximations, the numerical values set forth in the specific examples are reported as precisely as possible. All numerical values, however, inherently contain a range necessarily resulting from the standard deviation found in their respective testing measurements.

BRIEF DESCRIPTION OF THE FIGURES

Figure 1:
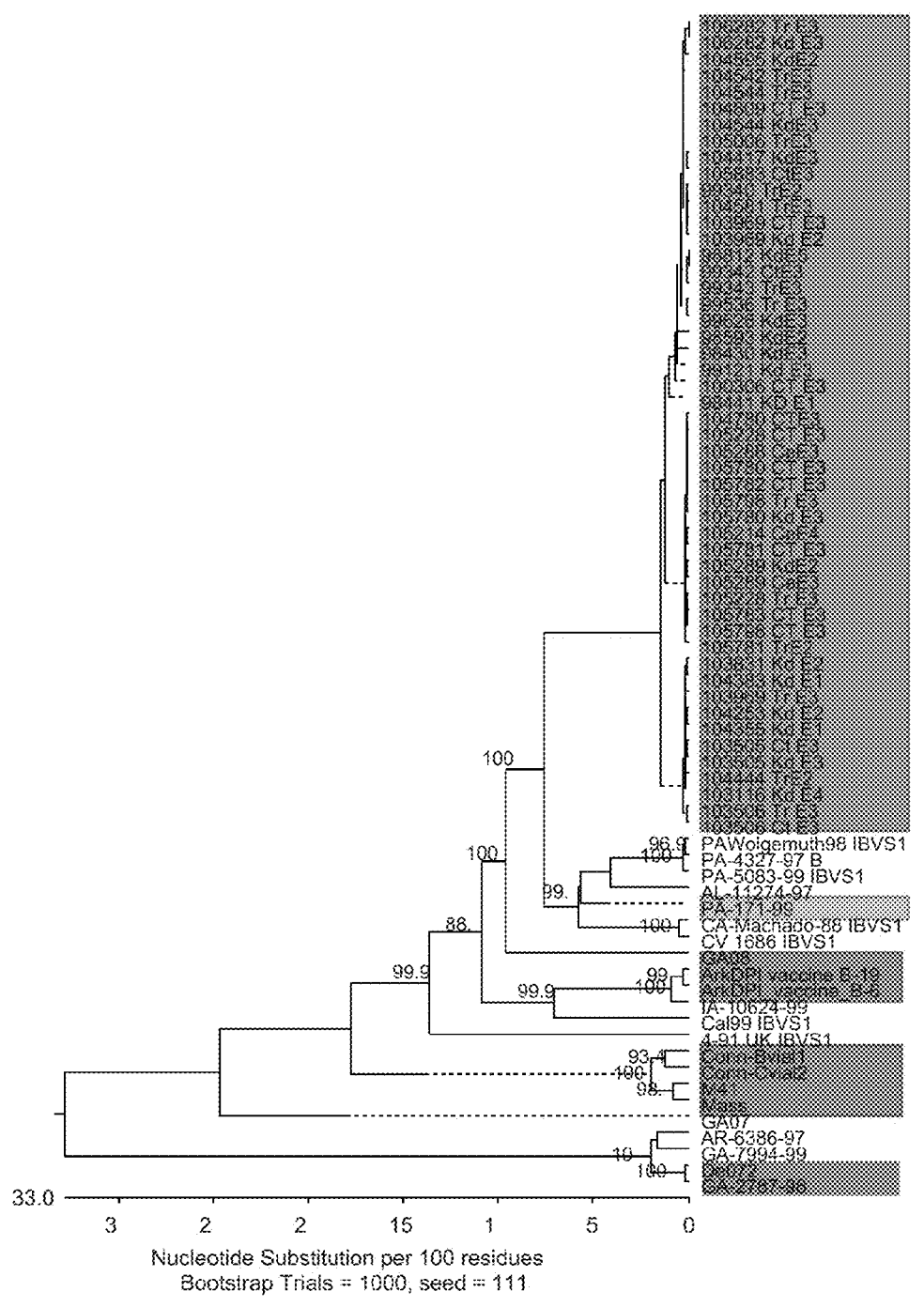

FIG. 1. Phylogenetic tree of S1 nucleotide sequences. The phylogenetic tree was generated following multiple alignment of the S1 nucleotide sequences (1-1,600 base pairs) using ClustalW (MegAlign, DNAStar, v.12). 1,000 bootstrap replicates were performed and values >70 are listed. GA-13 isolates are highlighted in the top block, commercial vaccines are highlighted in the bottom three blocks, and the isolate with the highest similarity, PA/171/99, is also highlighted.

FIG. 2. Clinical signs and macroscopic lesions observed at necropsy (at 36 days of age). The group identifications are as follows: NEG C=unvaccinated and unchallenged birds, CHALL C=unvaccinated birds challenged with GA13 at $10^4$ $EID_{50}$ per bird at 31 days of age, A/98=Ark/GA98 vaccination at 1 day of age, boosted with Ark/GA98 at 17 days of age and challenged at 31 days of age with GA13 at $10^4$ $EID_{50}$ per bird, A/98/08=Ark/GA98/GA08 vaccination at 1 day of age, boosted with Ark/GA98/GA08 at 17 days of age and challenged at 31 days of age with GA13 at $10^4$ $EID_{50}$ per bird, A/98/M=A/98/M vaccination at 1 day of age, boosted with Ark/GA98/MASS at 17 days of age and challenged at 31 days of age with GA13 at $10^4$ $EID_{50}$ per bird, A/98/08/M=Ark/GA98/GA08 vaccination at 1 day of age, boosted with Ark/GA98/MASS at 17 days of age and challenged at 31 days of age with GA13 at $10^4$ $EID_{50}$ per bird. Total numbers of birds in each group were as follows: NEG C=5, CHALL C=6, A/98=9, A/98/08=10, A/98/M=8, A/98/08/M=7.

FIG. 3. Tracheal lesion scores at 36 days of age. Scatter plot of individual tracheal lesion scores from histological evaluation of tracheas collected at necropsy (36 days of age, 5 days post challenge). Tracheal rings were individually scored on a scale of 1-4 where a score of 1=normal (no inflammatory cells, cilia is present, goblet cells or mucous glands are present with little to no mucous in the lumen); score 2=epithelial hyperplasia, presence of inflammatory cells, deciliation, attenuation of epithelium (healing), mucous in lumen, increased numbers of goblet cells or mucous glands; score 3=any type of necrosis, can have hemorrhage associated with necrosis or not. Inflammation present; score 4=any amount of ulceration (no matter the cause), can have hemorrhage associated with ulcer or not. Vertical capped lines represent the standard deviation while horizontal lines represent the mean for the group. Statistical analyses were performed using the Mann Whitney Rank Sum test. Significant differences between groups are designated by different letters at values $p<0.035$.

FIG. 4. Mean tracheal ciliostasis scores per group. Five tracheal sections were harvested from each bird in the upper, middle and lower trachea and ciliostasis scored on a scale of 0-4. Scores of 0=all cilia beating, 1=75-99% beating cilia, 2=50-75% beating cilia, 3=25-50% beating cilia, and 4=less than 25% beating cilia (based on the system described by Cook et al., 1999, *Avian Pathology;* 28:477-485).

FIG. 5. IBV Ct values at 36 days of age. Scatter plot of individual IBV real time RT-PCR cycle threshold (Ct) values from tracheal swabs taken at 36 days of age (5 days post GA-13 challenge). Vertical capped lines represent the standard deviation while horizontal lines represent the mean for the group. In this assay Ct values >35 are considered negative. The lower the Ct score, the higher the number of viral genome copies in a given sample. Statistical analyses were performed using one way Analysis of Variance (ANOVA). Significant differences between groups are designated by different letters at p=0.05.

Figure 6:
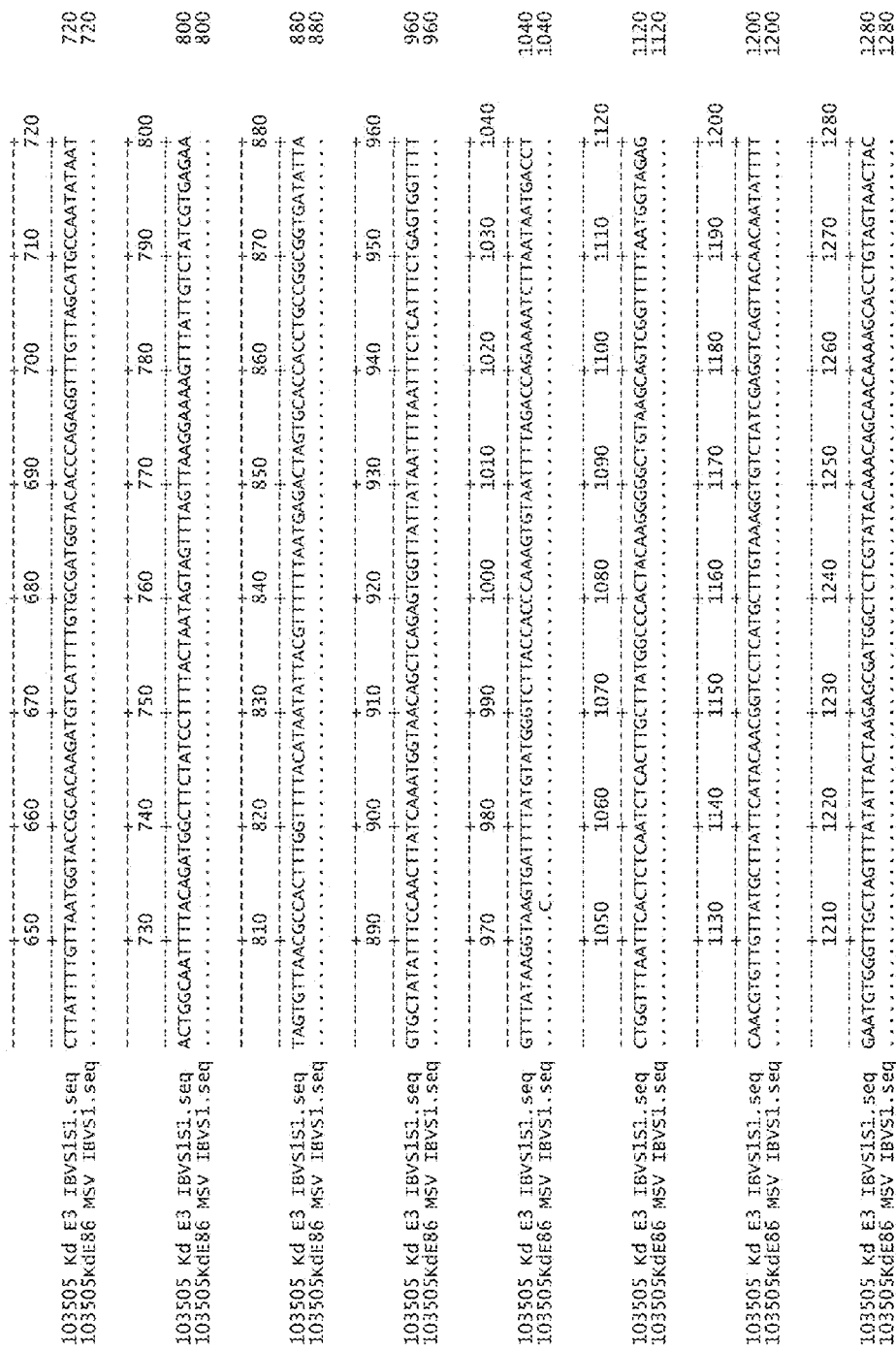

FIG. 6. Alignment of the full-length S1 glycoprotein (IBV S1) nucleic acid sequence of the IBV GA13 isolate 103505 Kd E3 (nucleotides 1-1,614 of SEQ ID NO:1) compared with the full-length S1 glycoprotein (IBV S1) nucleic acid sequence of the attenuated IBV GA13 103505KdE86 isolate (SEQ ID NO:3). ClustalW (Slow/Accurate, IUB) analysis.

Figure 7:
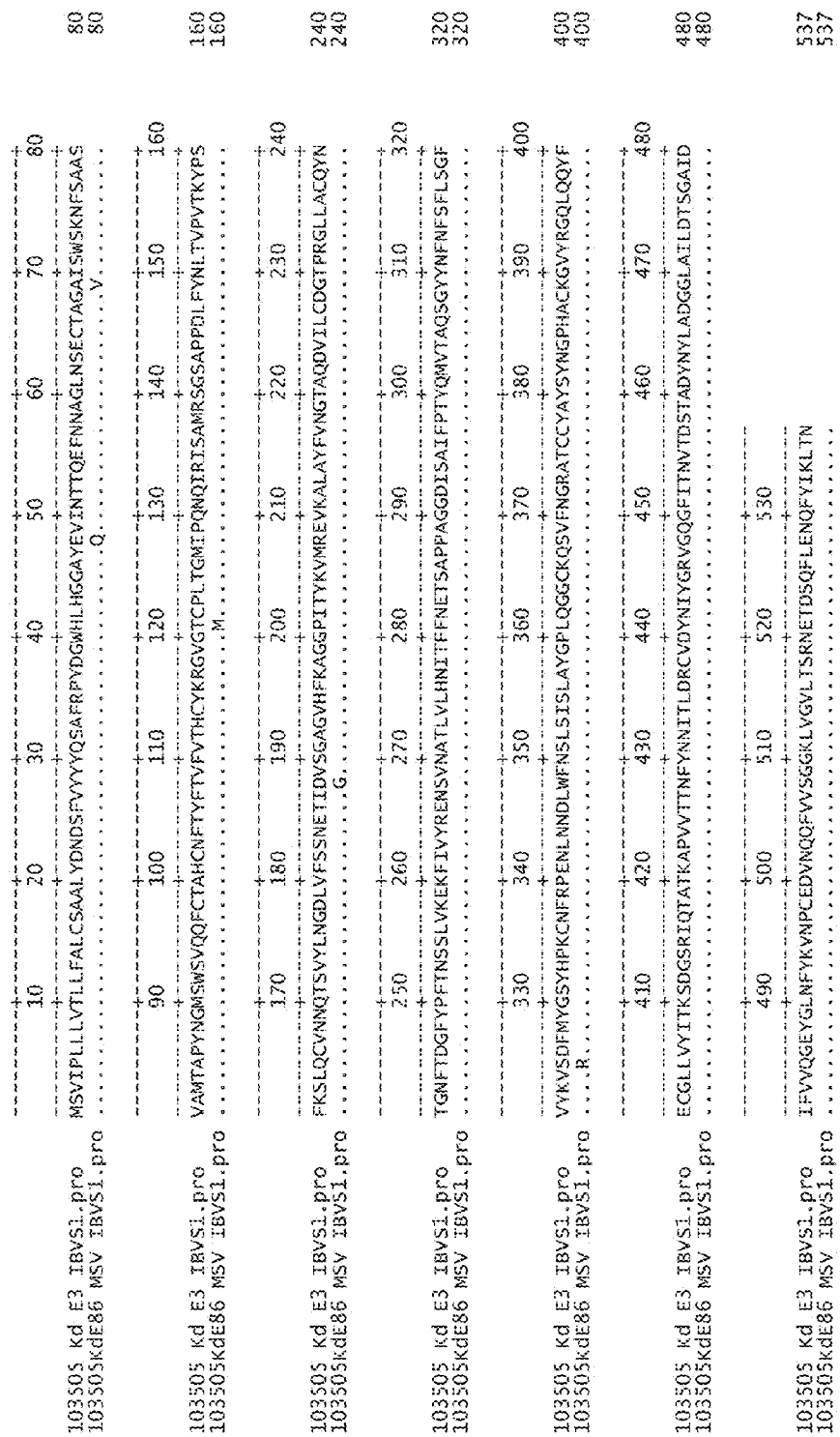

FIG. 7. Alignment of the deduced full-length S1 glycoprotein (IBV S1) amino acid sequence of the IBV GA13 isolate 103505 Kd E3 (residues 1-537 of SEQ ID NO:2) compared with the deduced full-length S1 glycoprotein amino acid sequence of the attenuated IBV GA13 103505KdE86 isolate (residues 1-537 of SEQ ID NO:4). ClustalW (Slow/Accurate, Gonnet) analysis.

FIG. 8. Tracheal lesion scores for GA13 E86 MSV. Mean tracheal lesion scores at 21 days of age and post-inoculation for groups 1) NEG=negative controls, 2) birds administered GA13 E86 MSV at $10^{5.5}$ $EID_{50}$ via eye drop per bird and 3) birds administered GA13 E86 MSV intratracheally at $10^{5.5}$ $EID_{50}$ per bird.

FIG. 9. Mean tracheal lesion scores on fixed tracheal rings (scale 1 to 4).

DETAILED DESCRIPTION OF ILLUSTRATIVE EMBODIMENTS

The present invention relates to new materials and methods in the field of poultry virology, particularly in the field of the infectious bronchitis virus (IBV). IBV is a highly contagious virus that causes respiratory, reproductive and renal disease in poultry. As is the case with many viruses, the IBV virus has multiple serotypes. More than 20 serotypes within IBV have been recognized worldwide (see, for example, Lee and Jackwood, 2000, *Arch Virol;* 145:2135-48). IBV can change rapidly in nature to yield variant viruses with new serotypes and causing disease in a susceptible host (Jackwood et al., 2005, *Avian Dis;* 49(4):614-8). Significant serotype-altered variants arise periodically and are suspected when vaccinated poultry flocks become symptomatic of the disease. The emergence of variant IBVs has been well documented, especially in areas of high density poultry production.

The present invention includes the identification, isolation, characterization, and attenuation of a new IBV variant, the IBV GA-13 variant, isolated from outbreaks of infectious bronchitis virus in vaccinated broilers in Georgia and North Carolina. This new GA-13 variant was genetically characterized by RT-PCR of the S1 subunit of the spike glycoprotein, sequenced, and compared to previous GA variants (GA07 and GA08), U.S. vaccines and other IBVs.

The present invention includes an isolated GA13 infectious bronchitis virus having the serotype and/or genotype of a GA13 viral isolate as described herein. Such a GA13 IBV viral isolate may include, for example, any of those described in Table 1, including, but not limited to, GA13 PDRC accession number 98430, GA13 PDRC accession number 98441, GA13 PDRC accession number 98593, GA13 PDRC accession number 98812, GA13 PDRC accession number 99121, GA13 PDRC accession number 99340, GA13 PDRC accession number 99342, GA13 PDRC accession number 99343, GA13 PDRC accession number 99536, GA13 PDRC accession number 99626, GA13 PDRC accession number 100306, GA13 PDRC accession number 103116, GA13 PDRC accession number 103505, GA13 PDRC accession number 103506, GA13 PDRC accession number 103831, GA13 PDRC accession number 103969, GA13 PDRC accession number 104011, GA13 PDRC accession number 104253, GA13 PDRC accession number 104316, GA13 PDRC accession number 104317, GA13 PDRC accession number 104354, GA13 PDRC accession number 104355, GA13 PDRC accession number 104383, GA13 PDRC accession number 104393, GA13 PDRC accession number 104417, GA13 PDRC accession number 104444, GA13 PDRC accession number 104542, GA13 PDRC accession number 104544, GA13 PDRC accession number 104580, GA13 PDRC accession number 104581, GA13 PDRC accession number 104595, GA13 PDRC accession number 104780, GA13 PDRC accession number 104809, GA13 PDRC accession number 105006, GA13 PDRC accession number 105214, GA13 PDRC accession number 105228, GA13 PDRC accession number 105288, GA13 PDRC accession number 105289, GA13 PDRC accession number 105290, GA13 PDRC accession number 105343, GA13 PDRC accession number 105780, GA13 PDRC accession number 105781, GA13 PDRC accession number 105782, GA13 PDRC accession number 105783, GA13 PDRC accession number 105798, GA13 PDRC accession number 105883, and/or GA13 PDRC accession number 106282. Such an isolate of GA13 may have been isolated from any of a variety of tissues, such as, for example, kidney (Kd), trachea (Tr), CT, or Ceca. Such an isolate may have been passaged one, two, three, four, five, or more times in an embryo prior to isolation. For example, an isolated may have been passaged in a tissue and/or embryo. Such an isolate of GA13 may be virulent, also referred to herein as "pathogenic." That is, poultry, such as chickens, when exposed to such an isolate exhibit one or more of the clinical symptoms of IBV infection.

In some embodiments, a GA13 isolate may be the IBV variant GA13 PDRC accession number 103505.

In some embodiments, a GA13 isolate may be the IBV variant GA13 PDRC accession number 103505 Kd E3, with the original tissue of isolation being kidney and the third embryo passage.

The present invention also includes attenuated isolates of a pathogenic GA13 IBV strain. Attenuated isolates demonstrate limiting virulence. Any of the various attenuation process known in the art may be used. For example, attenuated isolates may be obtained by passage through specific pathogen free (SPF) chicken embryos and/or by heat treatment. Examples of such attenuation processes include, but are not limited to, those described, for example, in WO 2009/143332 and U.S. Pat. No. 8,679,504 (each of which are hereby incorporated by reference in their entirety). For example, attenuated isolates may be obtained by passaging virulent isolates of the present invention in a culture on a suitable medium a sufficient number of times to reduce its pathogenicity while retaining its immunogenicity. A preferred medium for such passaging is a SPF embryonated egg. Inoculation of the eggs can be via the allantoic cavity, chorioallantoic membrane, yolk sac, amniotic cavity or even direct into the embryo. The virus can be passaged at regular intervals of from 7 hours up to 4 days. Commonly, passaging takes place between 16 to 36 hours, preferably every 24 hours. Alternatively, attenuation may also be achieved by passaging the isolate in avian cell culture, such as chick embryo kidney cells.

Attenuated GA13 IBV isolates include, but are not limited to, attenuated isolates of GA13 PDRC accession number 98430, GA13 PDRC accession number 98441, GA13 PDRC accession number 98593, GA13 PDRC accession number 98812, GA13 PDRC accession number 99121, GA13 PDRC accession number 99340, GA13 PDRC accession number 99342, GA13 PDRC accession number 99343, GA13 PDRC accession number 99536, GA13 PDRC accession number 99626, GA13 PDRC accession number 100306, GA13 PDRC accession number 103116, GA13 PDRC accession number 103505, GA13 PDRC accession number 103506, GA13 PDRC accession number 103831, GA13 PDRC accession number 103969, GA13 PDRC accession number 104011, GA13 PDRC accession number 104253, GA13 PDRC accession number 104316, GA13 PDRC accession number 104317, GA13 PDRC accession number 104354, GA13 PDRC accession number 104355, GA13 PDRC accession number 104383, GA13 PDRC accession number 104393, GA13 PDRC accession number 104417, GA13 PDRC accession number 104444, GA13 PDRC accession number 104542, GA13 PDRC accession number 104544, GA13 PDRC accession number 104580, GA13 PDRC accession number 104581, GA13 PDRC accession number 104595, GA13 PDRC accession number 104780, GA13 PDRC accession number 104809, GA13 PDRC accession number 105006, GA13 PDRC accession number 105214, GA13 PDRC accession number 105228, GA13 PDRC accession number 105288, GA13 PDRC accession number 105289, GA13 PDRC accession number 105290, GA13 PDRC accession number 105343, GA13 PDRC accession number 105780, GA13 PDRC accession number 105781, GA13 PDRC accession number 105782, GA13 PDRC accession number 105783, GA13 PDRC accession number 105798, GA13 PDRC accession number 105883, or GA13 PDRC accession number 106282 obtained by methods including, but not limited to, passage through embryonated eggs and/or heat treatment. Such an attenuated GA13 isolate includes, but is not limited to, attenuated isolates obtained by passage of a GA13 viral isolate through embryonated eggs obtained after, for example, with 10 or more passages, 20 or more passages, 50 or more passages, 70 or more passages, 80 or more passages, 85 or more passages, 90 or more passages, 95 or more passages, or 100 or more passages. Such an attenuated GA13 isolate includes, but is not limited to, attenuated isolates obtained by passage of a GA13 viral isolate through embryonated eggs obtained after, for example, about 10 passages, about 20 passages, about 50 passages, about 70 passages, about 80 passages, about 85 passages, about 90 passages, about 95 passages, or about 100 passages. Such an isolate may be obtained after, for example, about 3 passages (E3), about 6 passages (E6), 12 passages (E12), 16 passages (E16), 17 passages (E17), 20 passages (E20), 22 passages (E20), 37 passages (E37), 42 passages (E42), 52 passages (E52), 57 passages (E57), 62 passages (E62), 70 passages, (E70), 71 passages (E71), 86 passage (E86), 93 passages (E93), or any number of passages from 1 to 150 (EN, wherein N is an integer from 1 to 150).

In some embodiments, an attenuated GA13 isolate may be an attenuated isolate of GA13 PDRC accession number 103505. In some embodiments, such an attenuated isolate of GA13 PDRC accession number 103505 may be obtained by passage of GA13 PDRC accession number 103505 through embryonated eggs, for example, with 10 or more passages, 20 or more passages, 50 or more passages, 70 or more passage, 80 or more passages, 85 or more passages, 90 or more passages, 95 or more passages, or 100 or more passages. Such an attenuated GA13 isolate includes, but is not limited to, attenuated isolates obtained by passage of a GA13 viral isolate through embryonated eggs obtained after, for example, about 10 passages, about 20 passages, about 50 passages, about 70 passages, about 80 passages, about 85 passages, about 90 passages, about 95 passages, or about 100 passages. Such an isolate may be obtained after, for example, 3 passages (E3), 6 passages (E6), 12 passages (E12), 16 passages (E16), 17 passages (E17), 20 passages (E20), 22 passages (E20), 37 passages (E37), 42 passages (E42), 52 passages (E52), 57 passages (E57), 62 passages (E62), 70 passages, (E70), 71 passages (E71), 86 passages (E86), 93 passages (E93), or any number of passages from 1 to 150 (EN, wherein N is an integer from 1 to 150).

In some embodiments, an attenuated GA13 isolate may be an attenuated isolated of GA13 PDRC accession number 103505 Kd E3. In some embodiments, such an attenuated isolate of GA13 PDRC accession number 103505 Kd E3 may be obtained by passage of GA13 PDRC accession number 103505 Kd E3 through embryonated eggs, for example, with 10 or more passages, 20 or more passages, 50 or more passages, 70 or more passage, 80 or more passages, 85 or more passages, 90 or more passages, 95 or more passages, or 100 or more passages. Such an attenuated GA13 isolate includes, but is not limited to, attenuated isolates obtained by passage of a GA13 viral isolate through embryonated eggs obtained after, for example, about 10 passages, about 20 passages, about 50 passages, about 70 passages, about 80 passages, about 85 passages, about 90 passages, about 95 passages, or about 100 passages. Such an isolate may be obtained after, for example, 3 passages (E3), 6 passages (E6), 12 passages (E12), 16 passages (E16), 17 passages (E17), 20 passages (E20), 22 passages (E20), 37 passages (E37), 42 passages (E42), 52 passages (E52), 57 passages (E57), 62 passages (E62), 70 passages, (E70), 71 passages (E71), 86 passages (E86), 93 passages (E93), or any number of passages from 1 to 150 (EN, wherein N is an integer from 1 to 150).

In some embodiments, an attenuated GA13 isolate may be an attenuated isolated of GA13 PDRC accession number 103505 Kd E86, obtained after 86 passages of GA13 PDRC accession number 103505 Kd through embryonated eggs.

An IBV isolate of the present invention, pathogenic or attenuated, may be deposited with the American Type Culture Collection (ATCC®) 10801 University Boulevard, Manassas, Va. 20110-2209, USA. Such a deposit may be in accordance with the Budapest Treaty on the International Recognition of the Deposit of Microorganisms for the Purposes of Patent Procedure.

Avian infectious bronchitis virus strain GA-13 103505 Kd E86 was deposited with the American Type Culture Collection (ATCC®), 10801 University Boulevard, Manassas, Va. 20110-2209, USA on Mar. 15, 2017, in accordance with the Budapest Treaty on the International Recognition of the Deposit of Microorganism for the Purposes of Patent Procedure and assigned ATCC Designation PTA-124038.

The enveloped IBV virus has a single stranded-positive sense RNA genome that codes for the viral RNA-dependent RNA-polymerase, three major structural proteins (the nucleocapsid, membrane, and spike (S) proteins), and numerous regulatory proteins (Masters, 2006, *Adv Vir Res;* 66:193-292). The spike glycoprotein of IBV is translated as a precursor protein (So) and then cleaved into two subunits, the N-terminal S1 glycoprotein and the C-terminal S2 glycoprotein by host cell serine proteases. The S1 and S2 glycoproteins mediate cell attachment, virus-cell membrane fusion, and play an important role in host cell specificity, forming club shaped projections on the surface of the virus. The S1 glycoprotein induces virus-neutralizing and hemagglutination-inhibiting antibodies.

The IBV virus has multiple serotypes, with more than 20 serotypes within IBV recognized worldwide (Lee and Jackwood, 2000, Arch Virol; 145:2135-48). New variant strains arise due to rapid recombination, insertions, deletions, or point mutation events, predominantly in the S1 spike protein gene. Along with the use of serologic based tests, PCR and partial sequencing of the S1 gene can be used to group and type IBV isolates. The sequence from the hypervariable regions of the IBV S1 gene often correlates well with virus neutralization tests and can be reliably used to serotype an IBV isolate (Lee et al., 2003, J Vet Diagn Invest; 15:344-348). In the S1 subunit, three hypervariable regions (HVR) have been identified, located within amino acids 38-67, 91-141, and 274-387 (see, for example, Cavanagh et al., 1988, Virus Res; 11:141-150; Koch et al., 1990, J Gen Virol; 71:1929-1935; and Moore et al., 1997, Arch Virol; 142: 2249-2256).

The GA13 isolates described herein represent a new, genetically distinct group of IBVs that are not similar to previously known, endemic IBVs. Based on sequence analysis of the S1 region, including the hypervariable regions of S1, GA13 represents a new, unique S1 serotype and S1 genotype in comparison to previously known IBV S1 sequences.

The present invention includes IBV viral isolates with a nucleotide sequence encoding an S1 polypeptide of a S1 serotype and/or genotype defined by the GA13 isolate described herein. Such a nucleotide sequence may be a nucleotide sequence encoding an S1 polypeptide from a pathogenic isolate of GA13, including, but not limited to, any one of the pathogenic GA13 isolates described herein, or an attenuated isolate, including, but not limited to, any of those described herein. For example, the present invention includes polynucleotide sequences with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the polynucleotide sequence of SEQ ID NO:1 and/or SEQ ID NO:3. The present invention includes IBV viral isolates with a nucleotide sequence of SEQ ID NO:1. The present invention includes IBV viral isolates with a nucleotide sequence of SEQ ID NO:3.

The present invention includes IBV viral isolates with an S1 polypeptide encoded by such a nucleotide sequence. For example, an IBV isolated may have an S1 polypeptide with an amino acid sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the amino acid sequence of SEQ ID NO:2 and/or SEQ ID NO:4. The present invention includes an IBV viral isolate with an S1 polypeptide with an amino acid sequence of SEQ ID NO:2. The present invention includes an IBV viral isolate with an S1 polypeptide with an amino acid sequence of SEQ ID NO:4.

In some embodiments, the present invention includes a GA13 IBV variant having an S1 polypeptide with an amino acid sequence that includes any one, any two, any three, any four, or all five of the following amino acids residues: a glutamine at position 48; a valine at position 69; a methionine at position 121; a glycine at position 188; and/or an arginine at position 325.

The present invention includes a nucleotide sequence encoding an S1 polypeptide of a GA13 IBV isolate as described herein, including, for example, a polynucleotide sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the polynucleotide sequence of SEQ ID NO:1 and/or SEQ ID NO:3. The present invention includes a polynucleotide sequence of SEQ ID NO:1. The present invention includes a polynucleotide sequence of SEQ ID NO:3. Sequence identity may be determined, for example, using BLAST analysis. "BLAST analysis" is intended to mean the nucleotide or protein sequence analysis program available from the United States National Center for Biotechnology, and as described in more detail herein.

The present invention includes polynucleotide sequences that hybridize to the nucleotide sequence of SEQ ID NO:1 and/or SEQ ID NO:3, or a complement thereof, under various stringency conditions, and fragments thereof. Stringency conditions include, but are not limited to, moderate and high stringency. High stringency hybridization conditions may be, for example, 6×SSC, 5×Denhardt, 0.5% sodium dodecyl sulfate (SDS), and 100 µg/ml fragmented and denatured salmon sperm DNA hybridized overnight at 65° C. and washed in 2×SSC, 0.1% SDS at least one time at room temperature for about 10 minutes followed by at least one wash at 65° C. for about 15 minutes followed by at least one wash in 0.2×SSC, 0.1% SDS at room temperature for at least 3 to 5 minutes. The present invention includes polypeptides encoded by such hybridizing polynucleotide sequences.

A polynucleotide sequence may be DNA, RNA, or a modification thereof. A polynucleotide sequence may be single or double stranded, sense (positive) or antisense (negative) sequences.

Also included in the present invention are polynucleotide fragments. A polynucleotide fragment is a portion of an isolated polynucleotide as described herein. Such a portion may be several hundred nucleotides in length, for example about 100, about 200, about 300, about 400, about 500, about 600, or about 700, nucleotides in length. Such a portion may be about 10 nucleotides to about 100 nucleotides in length, including but not limited to, about 14 to about 40 nucleotides in length. Fragments of about 12 to about 100 nucleotides may be used as primers to, for example, amplify all or part of an IBV S1 gene or modify an IBV S1 gene by site-specific mutagenesis. Fragments of about 10 to about 30 nucleic acids can be used, for example, in single stranded forms, double stranded forms, short hairpin RNAs, microRNAs or small interfering RNAs to alter the expression of the an IBV S1 gene by RNA interference or other DICER-mediated mechanisms. Fragments of about 20 to about 1000 nucleotides can be used, for example, in a variety of blot-based assays, including dot blots, northern blots, southern blots, and in situ hybridization assays.

Also included in the present invention are complements of the polynucleotides described herein. As used herein, "complement" and "complementary" refer to the ability of two single stranded polynucleotides to base pair with each other, where an adenine on one polynucleotide will base pair to a thymine on a second polynucleotide and a cytosine on one polynucleotide will base pair to a guanine on a second polynucleotide. Two polynucleotides are complementary to each other when a nucleotide sequence in a polynucleotide base pairs with a nucleotide sequence in a second polynucleotide. For instance, 5'-ATGC and 5'-GCAT are complementary. Typically two polynucleotides are complementary if they hybridize under the standard conditions referred to herein.

The present invention includes polynucleotide sequences having a substitution of one, two, three, four, five, six, seven, eight, nine, ten, or more nucleotides from that of SEQ ID NO:1 and/or SEQ ID NO:3. The present invention also includes the polynucleotide sequences described herein in which codon usage has been adapted to optimize expression in a given host cell. For example, codon usage may be adapted to optimize for expression in host cells including, but not limited to, baculovirus, yeast, E. coli, poultry, or human cells. Such adaptation can be carried out by techniques know in the art.

The present invention provides a recombinant vector containing one or more of the nucleotide sequences described herein. Such a recombinant vector may also include other sequences such as expression control sequences, markers, amplifying genes, signal sequences, promoters, and the like, as is known in the art. Useful vectors for this purpose are plasmids, and viruses such as baculoviruses, paramyxovirus, coronavirus, herpes virus (for example, herpes virus of turkeys (HVT)) and pox viruses, for example, fowl pox virus, and the like. Such a vector may be an expression vector selected for expression in vitro or in vivo or expression in prokaryotic cells or eukaryotic cells. The nucleic acids of the present invention may be used to produce constructs that express antigens. Such antigens may be utilized, for example, to produce antibodies, which may be used for identifying field or laboratory isolates of the present invention.

The present invention also includes host cells transformed with a polynucleotide sequence described herein and host cells transformed with a recombinant vector described herein. The host cell may be, for example, a eukaryotic or a prokaryotic host cell. Suitable examples are E. coli, insect cell lines such as Sf-9, chicken embryo fibroblast (CEF) cells, chicken embryo kidney (CEK) cells, African green monkey Vero cells and the like.

The present invention includes polypeptides having an amino acid sequence of an S1 polypeptide of the S1 serotype and/or genotype defined by a GA13 isolate as described herein. Such an amino acid sequence may be from a pathogenic isolate of GA13 or an attenuated isolate of GA13, including, but not limited to, GA13 isolate 103505 KdE3 or an attenuated isolate thereof, including, but not limited to, attenuated GA13 isolate 103505 KdE86.

For example, the present invention includes a S1 polypeptide with an amino acid sequence with at least about 60% sequence identity, at least about 65% sequence identity, at least about 70% sequence identity, at least about 75% sequence identity, at least about 80% sequence identity, at least about 85% sequence identity, at least about 86% sequence identity, at least about 87% sequence identity, at least about 88% sequence identity, at least about 89% sequence identity, at least about 90% sequence identity, at least about 91% sequence identity, at least about 92% sequence identity, at least about 93% sequence identity, at least about 94% sequence identity, at least about 95% sequence identity, at least about 96% sequence identity, at least about 97% sequence identity, at least about 98% sequence identity, or at least about 99% sequence identity to the amino acid sequence of SEQ ID NO:2 and/or SEQ ID NO:4. For example, the present invention includes an S1 polypeptide with an amino acid sequence of SEQ ID NO:2. For example, the present invention includes an S1 polypeptide with an amino acid sequence of SEQ ID NO:4.

In some embodiments, the present invention includes a S1 polypeptide with an amino acid sequence that includes any one, any two, any three, any four, or all five of the following amino acids residues: a glutamine at position 48; a valine at position 69; a methionine at position 121; a glycine at position 188; and/or an arginine at position 325.

"Polypeptide" as used herein refers to a polymer of amino acids and does not refer to a specific length of a polymer of amino acids. Thus, for example, the terms peptide, oligopeptide, protein, and enzyme are included within the definition of polypeptide, whether naturally occurring or synthetically derived, for instance, by recombinant techniques or chemically or enzymatically synthesized. This term also includes post-expression modifications of the polypeptide, for example, glycosylations, acetylations, phosphorylations, and the like.

The present invention includes polypeptides having the amino acid sequence shown in SEQ ID NO:2 and/or SEQ ID NO:4, and truncations and fragments thereof. Truncations include, but are not limited to, amino acid sequences in which one, two, three, four, five, six, or more amino acids are removed from the amino terminus of the amino acid sequence and/or one, two, three, four, five, six, or more amino acids are removed from the carboxy terminus of the amino acid sequence. Fragments include, but are not limited to, for example, fragments having about 5, about 10, about 15, about 20, about 25, about 50, about 75, about 100, about 150, about 200, about 250, about 300, about 350, about 400, about 450, about 500, about 550, about 600, about 650, and about 700 consecutive amino acid residues of the sequence of SEQ ID NO:2. Fragments also include, for example, fragments of a size range of any combination of the above fragment sizes. Fragments include, but are not limited to, for example, fragments having at least 5, at least 10, at least 15, at least 20, at least 25, at least 50, at least 75, at least 100, at least 150, at least 200, at least 250, at least 300, at least 350, at least 400, at least 450, at least 500, at least 550, at least 600, at least 650, and at least 700 consecutive amino acid residues of SEQ ID NO:2.

The present invention includes polypeptides having an amino acid sequence with one, two, three, four, five, six, seven, eight, nine, ten, eleven, twelve, thirteen, fourteen, fifteen, sixteen, seventeen, eighteen, nineteen, twenty, or more amino acid changes from the amino acid sequence of SEQ ID NO:2 and/or SEQ ID NO:4. Such amino acid changes include, but are not limited to, conservative amino acid changes. As used herein, the term "conservative substitution" refers to the replacement of an amino acid residue by a structurally similar residue. Examples of conservative substitutions include the substitution of one hydrophobic residue such as isoleucine, valine, leucine or methionine for another, or the substitution of one polar residue for another, such as the substitution of arginine for lysine, glutamic for aspartic acids, or glutamine for asparagine, and the like.

The present invention includes polypeptides having an amino acid sequence with at least about 75%, at least about 80%, at least about 85%, at least about 86%, at least about 87%, at least about 88%, at least about 89%, at least about 90%, at least about 91%, at least about 92%, at least about 93%, at least about 94%, at least about 95%, at least about 96%, at least about 97%, at least about 98%, or at least about 99% amino acid sequence similarity with the amino acid sequence of SEQ ID NO:2 and/or SEQ ID NO:4.

As used herein, "structural similarity" refers to the identity between two polypeptides. Structural similarity is generally determined by aligning the residues of the two polypeptides to optimize the number of identical amino acids along the lengths of their sequences; gaps in either or both sequences are permitted in making the alignment in order to optimize the number of identical amino acids, although the amino acids in each sequence must nonetheless remain in their proper order. For example, polypeptides may be compared using the Blastp program of the BLAST 2 search algorithm, as described by Tatusova et al. (FEMS Microbiol Lett; 174; 247-250, 1999) and available on the world wide web at ncbi.nlm.nih.gov/BLAST/. In the comparison of two amino acid sequences using the BLAST search algorithm, structural similarity may be referred to by percent "identity" or may be referred to by percent "similarity." "Identity" refers to the presence of identical amino acids and "similarity" refers to the presence of not only identical amino acids but also the presence of conservative substitutions.

The present invention includes compositions of matter including or encoding an S1 polypeptide of the GA13 serotype and/or GA13 genotype as described herein. A composition of matter may be, for example, a virus, a polypeptide, or a nucleotide sequence.

The present invention includes antibodies that bind to a S1 polypeptide, as described herein, and various antibody fragments, also referred to as antigen binding fragments, which include only a portion of an intact antibody, generally including an antigen binding site of the intact antibody and thus retaining the ability to bind antigen.

For example, such an antibody, or antigen binding fragment thereof, may bind to a polypeptide having an amino acid sequence with at least 90% sequence identity, at least about 95% sequence identity to, at least about 98% sequence identity to, or about at least 99% sequence identity to SEQ ID NO:2 and/or SEQ ID NO:4. Such an antibody, or antigen binding fragment thereof, may bind to a polypeptide having the amino acid sequence of SEQ ID NO:2 and/or SEQ ID NO:4. Such an antibody, or antigen binding fragment thereof, may bind to a polypeptide including at least five, at least ten, at least eleven, at least twelve, at least thirteen, at least fourteen, at least fifteen, at least twenty, at least twenty five, at least thirty, at least forty, at least fifty, at least seventy-five, at least one hundred, at least two hundred, at least three hundred, at least four hundred, at least five hundred, at least six hundred, or at least seven hundred consecutive amino acid residues of SEQ ID NO:2 and/or SEQ ID NO:4.

In some embodiments, while binding to an amino acid sequence of an S1 polypeptide as described herein, or a fragment thereof, such an antibody may not bind to a previously known IBV isolate. Such a previously known isolates of IBV may include, for example, HN99, JAAS/04, N1/62, CA/557/03, CAV/CAV1686/95, CA/CA12495/98, CAV/CAV9437/95, Ark, Ark/ArkDPI/81, C2NDV, CU84074, CAV/CAV56b/91, CA/CA12495/98, Ark/Ark99/73, PP14/PP14/93, CAL99/CA1535/99, CAL99/NE15172/95, Holte/Holte/54, JMK/JMK/64, Gray/Gray/60, SE17/SE17/93, Iowa/Iowa609/56, B/D207/84, B/UK167/84, B/UK142/86, E/D3896/84, CAV/CA1737/04, DMV/5642/06, QX/IBVQX/99, 793B/4-91/91, Mass/H52, Mass/H120, Mass/Mass41/41, Mass/Beaudette, Conn/Conn46/51, FL/FL18288/71, DE/DE072/92, GA98/CWL470/98, GAD-utch/D1466/81, any of the GA07 or GA08 isolates described in WO 2009/143332 and U.S. Pat. No. 8,679,504, and/or any of the non GA13 isolates shown in the phylogenetic tree shown in FIG. 1.

In some embodiments, while binding to an S1 polypeptide having SEQ ID NO:4, or a fragment thereof, such an antibody may not bind to an S1 polypeptide having SEQ ID NO:2.

In some embodiments, while binding to an S1 polypeptide having SEQ ID NO:2, or a fragment thereof, such an antibody may not bind to an S1 polypeptide having SEQ ID NO:4.

Examples of antibody fragments include, for example, Fab, Fab', Fd, Fd', Fv, dAB, and F(ab')2 fragments produced by proteolytic digestion and/or reducing disulfide bridges and fragments produced from an Fab expression library. Antibodies include, but are not limited to, polyclonal antibodies and monoclonal antibodies. The antibodies of the present invention can be of any type (e.g., IgG, IgE, IgM, IgD, IgA and IgY), class (e.g., IgG1, IgG2, IgG3, IgG4, IgA1 and IgA2) or subclass of immunoglobulin molecule. Immunoglobulins can have both heavy and light chains. An array of IgG, IgE, IgM, IgD, IgA, and IgY heavy chains can be paired with a light chain of the kappa or lambda form.

The antibodies of the invention can be from any animal origin, including birds and mammals. In some embodiments, the antibodies are human, murine, rat, donkey, sheep, rabbit, goat, guinea pig, camel, horse, or chicken antibodies. As used herein, "human" antibodies include antibodies having the amino acid sequence of a human immunoglobulin and include antibodies isolated from human immunoglobulin libraries or from animals transgenic for one or more human immunoglobulins.

Monoclonal antibodies of the present invention can be obtained by various techniques familiar to those skilled in the art. For example, spleen cells from an animal immunized with a desired antigen are immortalized, commonly by fusion with a myeloma cell. Monoclonal antibodies can be isolated and purified from hybridoma cultures by techniques well known in the art. Other known methods of producing transformed B cell lines that produce monoclonal antibodies may also be used. In some embodiments, the antibody can be recombinantly produced, for example, produced by phage display or by combinatorial methods. Such methods can be used to generate human monoclonal antibodies.

Also included in the present invention are hybridoma cell lines, transformed B cell lines, and host cells that produce the monoclonal antibodies of the present invention; the progeny or derivatives of these hybridomas, transformed B cell lines, and host cells; and equivalent or similar hybridomas, transformed B cell lines, and host cells.

The present invention includes isolated viruses, polypeptides, polynucleotides, and antibodies. As used herein, "isolated" refers to material removed from its original environment (e.g., the natural environment if it is naturally occurring), and thus is altered "by the hand of man" from its natural state. Viruses, polypeptides, polynucleotides, antibodies, and compositions thereof of the present invention may be stored until use in any of a variety of forms. For example, such materials, including, but not limited to, attenuated viral material, may be lyophilized and may be rehydrated for use. In another embodiment, materials may be frozen.

The present invention includes kits employing one or more of the viruses, polypeptides, polynucleotides, and/or antibodies described herein. Such kits may provide for the administration of a polypeptide or polynucleotide of the present invention to an animal in order to elicit an immune response. Such kits may provide for the detection of a polypeptide, antibody or polynucleotide, for example, for the detection of IBV infection or exposure to an IBV agent in an animal. Kits of the present invention may include other reagents such as buffers and solutions needed to practice the invention are also included. Optionally associated with such container(s) can be a notice or printed instructions. As used herein, the phrase "packaging material" refers to one or more physical structures used to house the contents of the kit. The packaging material is constructed by well-known methods, preferably to provide a sterile, contaminant-free environment. As used herein, the term "package" refers to a solid matrix or material such as glass, plastic, paper, foil, and the like, capable of holding within fixed limits a polypeptide. Kits of the present invention may also include instructions for use. Instructions for use typically include a tangible expression describing the reagent concentration or at least one assay method parameter, such as the relative amounts of reagent and sample to be admixed, maintenance time periods for reagent/sample admixtures, temperature, buffer conditions, and the like.

In one embodiment, the present invention includes a process for the preparation of live attenuated infectious bronchitis vaccine from a poultry virus isolate herein. Such a process may include one or more of the steps of passaging a poultry virus isolate as described herein in a culture on a suitable medium for sufficient number of times to reduce its pathogenicity while retaining its immunogenicity, heat treating the passaged culture, and/or harvesting the attenuated materials, wherein the material is of the GA13 S1 serotype and/or S1 genotype as described herein.

The present invention includes a live attenuated infectious bronchitis vaccine of an attenuated IBV GA13 isolate, as described herein.

The present invention includes a live attenuated infectious bronchitis vaccine of the attenuate IBV GA 13 isolate 103505 KdE86, as described herein.

The viruses, polypeptides, polynucleotides, vectors, host cells, and compositions of the present invention may be administered to poultry or other animals to elicit an immune response to IBV virus and/or an IBV S1 polypeptide of the S1 serotype and/or genotype defined by the GA13 isolate. The immune response may or may not confer protective immunity. Such an immune response may result in a reduction or mitigation of the symptoms of future IBV infection. Such an immune response may prevent a future RSS infection in poultry. Such an immune response may be a humoral immune response, a cellular immune response, and/or a mucosal immune response. A humoral immune response may include an IgG, IgM, IgA, IgD, and/or IgE response. The determination of a humoral, cellular, or mucosal immune response may be determined by any of a variety of methods, including, but not limited to, any of those described herein.

Vaccination for IBV is common for most commercial chickens. The vaccines are usually modified-live virus vaccines delivered through mass aerosol applications. The serotypes used in vaccination are often selected based on what serotypes the birds may be exposed to in the field. There is very little cross-protection between different serotypes of IBV. Accordingly, it is an object of the present invention to provide immunological materials that do not result in significant clinical signs or lesions indicative of IBV disease. It is another object to provide immunological materials of low virulence. It is another object to provide immunological materials with no increase in virulence when back passaged. It is another object to provide immunological materials that prevent infection with virulent wild type strains of IBV.

The viruses, polypeptides, polynucleotides, vectors, host cells, and compositions of the present invention may be administered to poultry or other animals as vaccines that reduce the susceptibility to disease induced by IBV. With such administration, the materials do not result in significant clinical signs or lesions indicative of IBV infection. Such animals may demonstrate circulating antibodies to IBV and/or reduced symptoms of IBV. Such compositions of matter may serve as vaccines that protect the birds from disease induced by IBV.

Compositions and vaccines of the present invention may include, for example, water or culture medium. Such compositions and vaccines may include pharmaceutically acceptable carriers or diluents. Carriers include, for example, stabilizers, preservatives and buffers. Suitable stabilizers include, for example, SPGA, carbohydrates (such as sorbitol, mannitol, starch, sucrose, dextran, glutamate or glucose), proteins (such as dried milk serum, albumin or casein) or degradation products thereof. Suitable buffers include, for example, alkali metal phosphates. Suitable preservatives include, for example, thimerosal, merthiolate, and gentamicin. Diluents include, but are not limited to, water, aqueous buffer (such as buffered saline), alcohols, and polyols (such as glycerol).

Compositions of matter of the present invention may be substantially pure. As used herein, "substantially pure" will mean material essentially free of any similar macromolecules or other biological entities that would normally be found with it in nature. In some embodiments, the organisms used in such formulations are live. In some embodiments, the organisms, compositions, or vaccines may be lyophilized.

Immunogenic compositions and vaccines of the present invention may be administered to birds of any of a variety of avian species that are susceptible to IBV infection, including, but not limited to, poultry, birds of the order Galliformes, and exotic bird species. Birds of the order Galliformes include, but are not limited to, chickens, turkeys, grouse, quails, and pheasants. As used herein, poultry includes domesticated birds that are kept for the purpose of collecting their eggs, or killing for their meat and/or feathers. These most typically are members of the superorder Galloanserae (fowl), especially the order Galliformes (which includes, for example, chickens, quail, turkeys, and grouse) and the family Anatidae (in order Anseriformes), commonly known as "waterfowl" (including, for example, ducks, geese, and swans). Poultry may also include other birds which are killed for their meat, such as pigeons or doves or birds considered to be game, like pheasants.

"Poultry" is intended to embrace any breed of chicken, pheasant, emu, ostrich and other type of bird that is susceptible to infection by IBV. Chickens include, but are not limited to, hens, roosters, broilers, roasters, layers, breeders, the offspring of breeder hens, and layers. In some embodiments, the compositions of matter and methods of the present invention also apply to animals other than poultry that are susceptible to infection with IBV. As used herein, the term "susceptible to" means the possibility or actuality of a detrimental response to the referenced microorganism, such as, for example, reduced vigor or a failure to thrive, when compared to a non-susceptible individuals or groups, and/or one or more pathological state(s) indicative of an IBV infection, including, but not limited to, any of those described herein.

Compositions and vaccines of the present invention may be formulated for delivery by any of a variety of routes known in the veterinary arts, such as for example, mucosal, intranasal, intraocular, or oral administration. Compositions and vaccines of the present invention may be formulated for delivery to the respiratory mucosa and may be administered such that it is immediately or eventually brought into contact with the bird's respiratory mucosal membranes. Compositions and vaccines of the present invention may be formulated for delivery by any of a variety of modes known in the veterinary arts, such as for example, spraying or aerolizing.

An immunogenic composition or vaccine of the present invention may be administered by any suitable known method of inoculating birds including, but not limited to, nasally, ophthalmically, by eye drop, by injection, in drinking water, in the feed, by exposure, in ovo, maternally, and the like.

The immunogenic composition or vaccine may be administered by mass administration techniques such as by placing the vaccine in drinking water or by spraying the animals' environment. A composition may be administered by spraying an individual or the flock with a solution, such aerosol delivery may involve the administration of the composition incorporated in small liquid particles. Such spray-type particles may have a droplet size ranging from between about 10 to about 100 microns, more preferably, a droplet size from between about <1 to about 50 microns. For the generation of the small particles, conventional spray-apparatus and aerosol generators may be used, such as the commercially available spray generators for knapsack spray, hatchery spray and atomist spray. Administration through drinking water may be carried out using conventional apparatus. When administered by injection, the immunogenic composition or vaccine may be administered parenterally. Parenteral administration includes, for example, administration by intravenous, subcutaneous, intramuscular, or intraperitoneal injection.

A composition or vaccine of the present invention may be administered to birds before or after hatching. Birds may receive such a composition of vaccine at any of a variety of ages. With delivery after hatching, materials may be delivered, for example, about one week after hatching, about two weeks after hatching, about three weeks after hatching, about four weeks after hatching, about five weeks after hatching, about six weeks after hatching, or any range thereof. For in ovo administration, materials may be delivered about seventeen days of incubation, about eighteen days of incubation, about nineteen days of incubation, about twenty days of incubation, and any range thereof.

An immunogenic composition or vaccine of the present invention may further include one or more immunogens derived from other pathogens infectious to poultry. Such immunogens may be derived from, for example, Marek's disease virus (MDV), other serotypes of infectious bronchitis virus (IBV), including, but not limited to, any of those described herein, Newcastle disease virus (NDV), egg drop syndrome (EDS) virus, turkey rhinotracheitis virus (TRTV), poxvirus, or reovirus.

The viruses, polypeptides, polynucleotides, vectors, host cells, and antibodies of the present invention may be utilized in any of the commonly used methods for IBV detection, such as, for example, hemagglutination (HA) (Lashgari and Newman, 1984, *Avian Dis;* 28:435-443), hemagglutination inhibition (King and Hopkins, 1983, *Avian Dis;* 27:100-112), AGPT (Lohr, 1980, *Avian Dis;* 24:463-467; and Lohr 1981, *Avian Dis;* 25:1058-1064), and RT-PCR (Kwon et al., 1993, *Avian Dis;* 37:194-202).

The present invention also includes methods for the detection of IBV isolates, the identification of IBV serotypes, the detection of IBV genotypes, and the detection of antibodies to IBV, including the detection of an IBV infection or the detection of previous exposure of an animal to IBV, wherein the IBV virus is of the S1 serotype and/or genotype defined by a GA13 isolate described herein. Such a method may employ determining that an antisera sample includes antibodies that specifically bind to a polypeptide of the present invention. Such a method may employ detecting the hybridization of a polynucleotide of the present invention to a sample, preferably under high stringency conditions. Such a method may employ producing a polymerase chain reaction (PCR) amplification, where the resultant amplicon demonstrates a sequence similar to a nucleotide sequence of the present invention. Such a method may employ producing a polymerase chain reaction (PCR) amplification utilizing a primer pair described herein. The polypeptides, polynucleotides, and/or antibodies may be labeled with one or more of the detectable markers known to the skilled artisan. In some aspects, the polypeptides, polynucleotides, and/or antibodies may be bound to a solid substrate.

Antibodies may be detected by any of a variety of methods, including, but not limited to, the methods described herein and any suitable method available to the skilled artisan. Immunoassays that can be used include, but are not limited to, competitive and non-competitive assay systems using techniques such as BIAcore analysis, FACS (Fluorescence activated cell sorter) analysis, immunofluorescence, immunocytochemistry, Western blots, radio-immunoassays, ELISA (enzyme linked immunosorbent assay), "sandwich" immunoassays, immunoprecipitation assays, precipitin reactions, gel diffusion precipitin reactions, immunodiffusion assays, agglutination assays, complement-fixation assays, immunoradiometric assays, fluorescent immunoassays, protein A immunoassays, to name but a few. Such assays are routine and well known in the art.

In some embodiments, primers, including, but not limited to any of those described herein, may be used in PCR to amplify the nucleotide sequence encoding a S1 glycoprotein from a sample, and the products compared via sequence analysis or hybridization, to nucleic acid sequence described herein, to identify an IBV virus of the S1 serotype and/or genotype defined by the GA13 isolate.

The present invention includes a method of detecting an infectious bronchitis virus (IBV) in a sample, the method including identifying in the sample a nucleotide sequence as described herein. For example, the present invention includes a method of detecting an infectious bronchitis virus (IBV) in a sample, the method including identifying in the sample a nucleotide sequence having at least 90%, at least 91%, at least 92%, at least 93%, at least 94%, at least 95%, at least 96%, at least 97%, at least 98%, or at least 99% sequence identity to SEQ ID NO:1. The present invention includes a method of detecting an infectious bronchitis virus (IBV) in a sample, the method including identifying in the sample a nucleotide sequence having SEQ ID NO:1 and/or SEQ ID NO:3.

In some embodiments, the present invention includes a method of detecting an infectious bronchitis virus (IBV) in a sample, the method including identifying in the sample an amino acid sequence having at least 90%, at least 91%, at least 92%, at least 93%, at least 94%, at least 95%, at least 96%, at least 97%, at least 98%, or at least 99% sequence identity to SEQ ID NO:2 and/or SEQ ID NO:4. The present invention includes a method of detecting an infectious bronchitis virus (IBV) in a sample, the method including identifying in the sample an amino acid sequence having SEQ ID NO:2 and/or SEQ ID NO:4.

Any of the diagnostic methods of the present invention may include the additional step of providing a report or print out of the results. The sample may be any sample in which IBV antibodies, viruses, antigens, or nucleotides are present, for example, a blood, serum or tissue sample. Such methods and kits may also provide for the detection of infectious IBV agents in environmental samples.

While the invention has been described in connection with specific embodiments, it will be understood that it is capable of further modifications and the appended Claims are intended to cover any variations, uses, or adaptations of the invention following, in general, the principles of the invention and including such departures from the present disclosure as come within known or customary practice within the art to which the invention pertains and as may be applied to the essential features hereinbefore set forth whether now existing or after arising.

The present invention is illustrated by the following examples. It is to be understood that the particular examples, materials, amounts, and procedures are to be interpreted broadly in accordance with the scope and spirit of the invention as set forth herein.

EXAMPLES

Example 1

Isolation and Characterization of Infectious Bronchitis Virus GA-13

This example describes the isolation, characterization and pathogenicity of a variant infectious bronchitis virus, GA-13, isolated in 2013 and 2014 from more than 47 field cases submitted by 6 companies in Georgia and North Carolina. All isolations were from bronchitis-vaccinated commercial broilers exhibiting mild to moderate respiratory disease. The primary submitting complaint was airsacculitis. Genetic, serologic and pathogenicity studies were performed as well as an evaluation of several commercial vaccines in a protection study. Nucleotide sequences of the full length S1 subunits were analyzed by a BLAST database search as well as phylogenetic analysis to determine the most closely related IBVs and revealed an 89.3% similarity to the nephrotropic PA/171/99 (isolated from layers in PA in 1999). The analysis also revealed the highest similarity to a US commercial IBV vaccine was 82.4% to GA-08 followed by 80.4% MASS. The GA-13 variant was pathogenic in 2-wk-old broilers inducing mild to moderate respiratory signs in 53% of experimentally infected chickens and airsacculitis in 43% of the birds compared to the negative controls. The GA-13 variant appears to be more respirotropic despite its genetic similarity to nephrotropic isolates. In addition, current commercial vaccines do not appear to provide full protection against challenge with the GA-13 variant.

Infectious bronchitis virus (IBV) is a highly contagious disease in chickens and can result in clinical diseases affecting the respiratory, renal and reproductive tracts (see, for example, Cavanagh, D., and S. A. Naqi. Infectious bronchitis. In: Diseases of Poultry, 11th ed. Y. M. Saif, H. J. Barnes, J. R. Glisson, A. M. Fadley, L. R. McDougald, and D. E. Swayne, eds. Iowa State University Press, Ames, Iowa pp. 101-119, 2003). The emergence of variant IBVs has been well documented, especially in areas of high density poultry production (see, for example, Lee and Jackwood, 2001, *Virus Res;* 80:33-39; Jackwood et al., 2007, *Avian Dis;* 51:527-533; and Gelb et al., 2013, *Avian Dis;* 57:65-70).

In 2013 and 2014 an outbreak of infectious bronchitis virus in vaccinated broilers in Georgia and North Carolina resulted in the isolation of a new IBV variant at the Poultry Diagnostic and Research Center at the University of Georgia. The viruses were isolated from birds with clinical signs ranging from mild to moderate snicking, rales, and in some cases increased mortality. The most common lesion observed on necropsy was airsacculitis and less commonly, pneumonia. Condemnation rates in affected flocks were significantly affected. The virus was isolated from tracheas, kidneys and/or cecal tonsils in SPF embryos and produced urate deposits in the kidneys of most embryos and minimal embryo mortality.

In this example, the isolation of a new variant, GA-13, from 47 diagnostic submissions of IBV during 2013-2014 is described. The isolates were genetically characterized by RT-PCR of the S1 subunit of the spike glycoprotein, sequenced, and compared to previous GA variants (GA07 and GA08), U.S. vaccines and other IBVs in the database. Serologic relatedness of the virus with the PA/171/99 (the highest match in the database) as well as with Mass and GA-08 (the most similar vaccine strains) was examined. In addition, the pathogenicity of the virus in commercial broilers was evaluated. In addition, a vaccine challenge study was performed to determine if currently available commercial vaccines would provide protection against challenge with the GA-13 variant.

Materials and Methods

Clinical samples and viruses. IBVs used in this study were isolated from tracheas, kidneys and/or cecal tonsils submitted to the Poultry Diagnostic and Research Center for virus isolation and characterization from vaccinated commercial broilers exhibiting respiratory signs. Virus isolation was performed in 9-11-day-old specific pathogen free (SPF) embryos as previously described (Gelb Jr, J. & Jackwood, M. W. Infectious bronchitis virus. In: In: A Laboratory Manual for the isolation, identification, and characterization of avian pathogens, 5th ed. L. Dufour-Zavala, D. E. Swayne, J. R. Glisson, J. E. Pearson, W. M. Reed, M. W. Jackwood & P. Woolcock, eds. American Association of Avian Pathologists, Kennett Square, Pa. pp. 146-149, 2008).

Embryos were checked daily for viability. Allantoic fluid was harvested from viable embryos at 48-72 hours post inoculation and evaluated for hemagglutination of chicken red blood cells (CRBCs) following treatment with neuraminidase as previously described (Ruano et al., 2000, Avian Dis; 44:99-104). On the 7th day post-inoculation, embryos were opened and evaluated for typical lesions associated with IBV such as stunting, curled toes, clubbed down and kidney urates. Allantoic fluid from embryo passages with mortality or lesions consistent with IBV was evaluated by RT-PCR for the presence of IBV RNA. Field isolates analyzed in this study are listed in Table 1.

TABLE 1

GA-13 IBV isolates.

| Isolate ID | Date of submission | State[A] | Age of bird in weeks | Tissue/embryo passage of isolation[B] |
|---|---|---|---|---|
| 98430 | Apr. 1, 2013 | GA | 4.6 | Kd E2, Tr E2 |
| 98441 | Apr. 2, 2013 | GA | 5.3 | Kd E1 |
| 98593 | Apr. 11, 2013 | GA | 6.1 | Kd E2 |
| 98812 | Apr. 25, 2013 | GA | 5 | Kd E5 |
| 99121 | May 9, 2013 | GA | 5.2 | Kd E3 |
| 99340 | May 22, 2013 | GA | 5.1 | Tr E2 |
| 99342 | May 22, 2013 | GA | 7.4 | Tr, Ct, Kd E3 |
| 99343 | May 22, 2013 | GA | 6.0 | TrE3 |
| 99536 | Jun. 4, 2013 | GA | 5.4 | Tr E3 |
| 99626 | Jun. 10, 2013 | GA | 0 | Kd E3 |
| 100306 | Jul. 18, 2013 | GA | 6.3 | Kd E2, CT E3 |
| 103116 | Jan. 9, 2014 | GA | 6.1 | Kd E3 |
| 103505 | Jan. 30, 2014 | GA | 6.3 | Kd E3, Ct E3 |
| 103506 | Jan. 30, 2014 | GA | 6.0 | Tr E3, Ct E3 |
| 103831 | Feb. 14, 2014 | GA | 6.4 | Kd E1 |
| 103969 | Feb. 19, 2014 | GA | 6.1 | Kd E2, CT E3, Tr E2 |
| 104011 | Feb. 21, 2014 | GA | 6.1 | Kd E2 |
| 104253 | Mar. 3, 2014 | GA | 6.0 | Kd E2 |
| 104316 | Mar. 6, 2014 | GA | 5.0 | Kd E3 |
| 104317 | Mar. 6, 2014 | GA | 6.0 | Kd E3, Tr E3 |
| 104354 | Mar. 10, 2014 | GA | 5.6 | Tr E3, Kd E3 |
| 104355 | Mar. 10, 2014 | GA | 6.4 | Kd E1, Tr E3 |
| 104383 | Mar. 12, 2014 | GA | 6.6 | Kd E1 |
| 104393 | Mar. 13, 2014 | GA | 6.0 | Kd E1, Tr E3 |
| 104417 | Mar. 14, 2014 | GA | 6.3 | Kd E3 |
| 104444 | Mar. 17, 2014 | GA | 5.3 | Tr E2 |
| 104542 | Mar. 18, 2014 | GA | 5.5 | Tr E3 |
| 104544 | Mar. 18, 2014 | GA | 6.4 | Tr E3, Kd E3 |
| 104580 | Mar. 20, 2014 | GA | 5.3 | Kd E1 |
| 104581 | Mar. 20, 2014 | GA | 5.6 | Tr E3 |
| 104595 | Mar. 21, 2014 | GA | 6.1 | Kd E2 |
| 104780 | Apr. 8, 2014 | NC | 7.1 | CT E3 |
| 104809 | Apr. 10, 2014 | GA | 7.1 | CT E3 |
| 105006 | Apr. 18, 2014 | GA | 7.1 | Tr E3 |
| 105214 | Apr. 29, 2014 | NC | 6.6 | Ceca E4 |
| 105228 | Apr. 30, 2014 | NC | 7.0 | CT E3, Tr E3 |
| 105288 | May 2, 2014 | NC | 6.6 | Ceca E3 |
| 105289 | May 2, 2014 | NC | 6.6 | Kd E2, ceca E3 |
| 105290 | May 2, 2014 | NC | 4.6 | Kd E2, Tr E3 |
| 105343 | May 7, 2014 | NC | 3.6 | Tr E3 |
| 105780 | May 28, 2014 | NC | 9.0 | Kd E3, CT E3 |
| 105781 | May 28, 2014 | NC | 6.4 | Tr E2, CT E3 |
| 105782 | May 28, 2014 | NC | 6.0 | CT E3 |
| 105783 | May 28, 2014 | NC | 5.5 | CT E3 |
| 105798 | May 28, 2014 | NC | 6.1 | Tr E3, CT E3 |
| 105883 | May 30, 2014 | GA | 5.4 | CT E3 |
| 106282 | Jun. 13, 2014 | NC | 5.2 | Tr E3, Kd E3 |

[A]State of isolation, GA = Georgia and NC = North Carolina
[B]Tr = trachea, Kd = kidney, CT = cecal tonsils; embryo passages designated as E1 = first embryo passage, E2 = second embryo passage or E3 = third embryo passage GA/99340/2013 was selected as a representative isolates for in vivo pathogenicity testing and propagated in 10-day-old embryonated specific pathogen free (SPF) chicken eggs via the chorioallantoic sac (CAS) and incubated at 37° C. with humidity. Allantoic fluid was collected from the embryos at 48-72 hours post inoculation and stored at −80° C. The titer was calculated using the method of Reed and Muench as previously described (Gelb Jr, J. & Jackwood, M. W. Infectious bronchitis virus. In: In: A Laboratory Manual for the isolation, identification, and characterization of avian pathogens, 5th ed. L. Dufour-Zavala, D. E. Swayne, J. R. Glisson, J. E. Pearson, W. M. Reed, M. W. Jackwood & P. Woolcock, eds. American Association of Avian Pathologists, Kennett Square, Pa. pp. 146-149, 2008; and Villegas, P. Titration of biological suspensions. In: A Laboratory Manual for the isolation, identification, and characterization of avian pathogens, 5th ed. L. Dufour-Zavala, D. E. Swayne, J. R. Glisson, J. E. Pearson, W. M. Reed, M. W. Jackwood & P. Woolcock, eds. American Association of Avian Pathologists, Kennett Square, Pa. pp. 217-221, 2008).

RNA extraction and RT-PCR. Total RNA was extracted from allantoic fluid using the RNeasy kit (Qiagen Inc., Valencia, Calif.) per the manufacturer's instructions. The cDNA corresponding to the S1 glycoprotein gene was produced by RT-PCR using the Superscript III one-step RT-PCR kit (Invitrogen Life Technologies, Grand Island, N.Y.) per manufacturer's instructions with previously published S1 primers, NEWS1OLIGO5' and S1Deg3', (Lee et al., 2000, Avian Dis; 44:650-654). The primers amplified a 1,750 base pair product that was separated on a 1.0% agarose gel, stained with ethidium bromide, and visualized with an ultraviolet transilluminator. The fragments were excised, purified with the QIAEX II gel extraction kit (Qiagen Inc.) per manufacturer's instructions, eluted in diethylpyrocarbonate-treated water, and stored at −80° C. until sequenced.

Direct nucleotide sequencing of amplified products. Gel-purified PCR products were sequenced by Sanger sequencing on an ABI 3700 automated sequencer (Applied biosystems Life Technologies, Grand Island, N.Y.) at the Georgia Genomics Facility (The University of Georgia, Athens, Ga.). PCR primers NEWS1OLIGO5' and S1Deg3' were used for sequencing, as well as, internal primers IBVPAf 5'GTTTCAGGYGCAGGTGTTCA3' (SEQ ID NO:5) and IBVPAr 5'ACCACTCTGAGCTGTTACCA3' (SEQ ID NO:6) to complete sequencing. Sequencing primers IBVPAf and IBVPAr were constructed based on the S1 sequence of IBV PA/171/99 (GenBank Accession AF419314) using Primer Select (Lasergene, v.12.0, DNASTAR, Madison, Wis.).

Sequence analysis. Nucleotide and protein sequences were analyzed by BLASTN and BLASTP at the National Center of Biotechnology Information (see the worldwide web at ncbi.nlm.nih.gov/BLAST/). Sequences with the highest similarity from the BLAST analyses were included in the multiple alignments and phylogenetic analyses. Nucleotide and predicted amino acid sequence analysis, as well as, multiple alignments of the S1 gene and protein were performed using CLUSTALW in MegAlign (Lasergene, v. 12.0, DNASTAR). Phylogenetic analysis was performed followed by 1,000 bootstrap replicates. Nucleotide and amino acid sequences of reference isolates used in the analysis were obtained from GenBank and had the following accession numbers: PA/171/99-AF419314, PAWolgemuth98-AF305595, PA-4327-97 [AY789944], PA-5083-99 [AY789945], AL-11274-97 [AF510565], CA-Machado-88 [AF41931], CV1686 [AF027511], GA08 [GU301925], Ark DPI vaccine B-19-[JQ660957], Ark DPI vaccine B-6 [GQ484958], IA-10624-99 [AF520607], Cal-99 [DQ912832], 4-91 UK [JN192154], Conn-Bvial1 [EU283057], Conn-Cvial2 [EU283062], M41[AY851295], Mass VX [EU359657], GA07-60173 [JN160805], AR-6386-97 [AF274436], GA-7994-99 [AF338717], De072 VX [AF274435], and GA-2787-98 [AF274438].

Pathogenicity of GA/99340/2013. Fifty-two commercial broiler chicks (vaccinated in ovo with HVT-SB1) were received at day of hatch, randomly divided into 4 groups of 10 birds each and housed in positive pressure Horsfall isolation units. The chicks were given non-medicated broiler starter feed and water ad libitum and monitored twice daily. At 2 weeks of age, 12 birds (3 from each unit) were removed and bled for serology. Three groups of 10 birds each were challenged intratracheally with 100 µl of $10^{4.5}$ $TCID_{50}$ of isolate GA/99340/2013. One group of 10 birds served as the negative controls and was not challenged. Birds were monitored twice daily for mortality and appearance of clinical signs. Prior to $CO_2$ gas euthanasia at 5 days post challenge, lacrimal fluid was collected from each bird using sodium chloride as a mild local irritant, in the method previously described (Toro et al., 1993, Avian Dis; 37:60-66). RNA was extracted from the lacrimal fluid swabs and real-time reverse transcriptase polymerase chain reaction (RT-PCR) with a TAQMAN® probe was performed as previously described (Callison et al., 2006, J Virol Methods; 138:60-65). Kidneys and tracheas were taken from each bird, placed in 10% neutral buffered formalin, routinely processed, stained with hematoxylin and eosin, and examined by light microscopy. Tracheas were not opened at necropsy in order to preserve their integrity for histological evaluation. Each trachea was scored on a scale from 1 to 4 based on the presence of epithelial hyperplasia, lymphocyte infiltration and epithelial deciliation.

Vaccination challenge experiment. The vaccine challenge experiment was performed in 1-day-old commercial broilers. Commercial vaccines used in this study were selected based on their similarity to GA13 as well as those used in a vaccination program within a company experiencing problems with GA13. Treatment groups are outlined in Table 2. Seventy-five, 1-day-old commercial broiler chicks were used in this study. Sixty chicks were randomly divided into 6 groups of 10 birds each and placed in positive pressure Horsfall isolation units. The remaining birds were bled for IBV serology. Group 1 was unvaccinated and unchallenged, group 2 received GA-13 challenge on day 31, group 3 was vaccinated by eyedrop with 1× dose of Ark and GA98 commercial vaccines on day 1 and 17, group 4 was vaccinated by eyedrop with 1× dose of Ark, GA98 and GA08 commercial vaccines on days 1 and 17, group 5 was vaccinated by eyedrop with 1× dose of Ark, GA98 and Mass commercial vaccines on days 1 and 17, and group 6 was vaccinated by eyedrop with 1× dose of Ark, GA98 and GA08 at day 1 and Ark, GA98 and Mass at day 17. Groups 2-6 were challenged intratracheally on day 31 with $10^4$ $EID_{50}$ GA/103505 KdE7/2014. Birds were monitored twice daily for clinical signs and euthanized 5 days post challenge (36 days of age) for necropsy and sample collection. Tracheal swabs were collected by rRT-PCR, tracheal rings (below the swab site) were collected for ciliostasis scoring and another set for histopathology and scoring.

TABLE 2

Treatment groups in vaccination/protection study.

| Group | Vaccination Day 1 | Vaccination Day 17 | CHALLENGE Day 31 |
|---|---|---|---|
| 1 | None | None | None |
| 2 | None | None | GA13 |
| 3 | Ark/GA98 | Ark/GA98 | GA13 |
| 4 | Ark/GA98/GA08 | Ark/GA98/GA08 | GA13 |
| 5 | Ark/Ga98/Mass | Ark/GA98/Mass | GA13 |
| 6 | Ark/GA98/GA08 | Ark/GA98/Mass | GA13 |

Results

Analysis of S1 gene sequence. IBV strains related to GA-13 isolates were identified in the BLASTn search and included in the phylogenetic analysis (FIG. 1). The nucleotide sequence of the S1 glycoprotein gene for the GA-13 isolates was most similar to PA-191-99 at 89.3%. However, they belong to a separate clade with a bootstrap confidence level of 100 indicating that they are not genetically related (FIG. 1). The IBV GA-08 vaccine was the most related vaccine strain at 82.4% similarity followed by Mass at 80.4% similarity. All GA-13 isolates were at least 98% similar to each other.

Pathogenicity in commercial broilers. At day 3 post challenge, snicking and head shaking were observed in all three units containing challenged birds. These clinical signs continued through day 5 at which time all birds were humanely euthanized and necropsied. Prior to necropsy, 16 out of the 30 challenged birds were exhibiting clinical signs ranging from snicking to mild rales; of these birds, 8 had mild sudsy airsacculitis upon necropsy. Additionally, 5 birds from challenged groups that did not have observable clinical signs had mild airsacculitis at necropsy, bringing the total of birds affected with airsacculitis to 13 out of 30 birds in the challenged group. No other gross lesions were observed in the challenged birds and no gross lesions were observed in the group of 10 negative controls.

All tracheas (30/30) in the challenged group had mild to moderate lymphoplasmacytic and heterophilic tracheitis with individual cell necrosis and marked deciliation. Some tracheas also had mucosal congestion, mild hemorrhages in the lamina propria and hyperplasia of mucous glands. All tracheas from challenged group scored 3. Tracheas (10/10) in the negative control group had minimal lymphocytic infiltration and small amounts of mucus in the lumen; all tracheas from the negative controls scored 2.

All kidneys (10/10) in the control group had focal to multifocal small lymphocytic infiltrates in the interstitium and some urate deposition in tubules of the medullary cone and in distal tubules. All kidneys from the control group had score 1. Most kidney sections in the challenged group (27/30) had similar mild lesions like seen in the control group, but three sections had mild to moderate lymphocytic infiltration in the interstitium with some tubular effacement. Twenty-seven sections scored 1, two sections scored 2 and one section scored 3.

Challenge virus was detected by real-time RT-PCR in lacrimal fluid from all of the GA-13 challenged birds, with cycle threshold (Ct) values ranging from 16.3 to 20.5 and an average Ct value of 19.1. Identity of the challenge isolate was confirmed by amplification and sequencing of the S1 gene.

Figure 3:
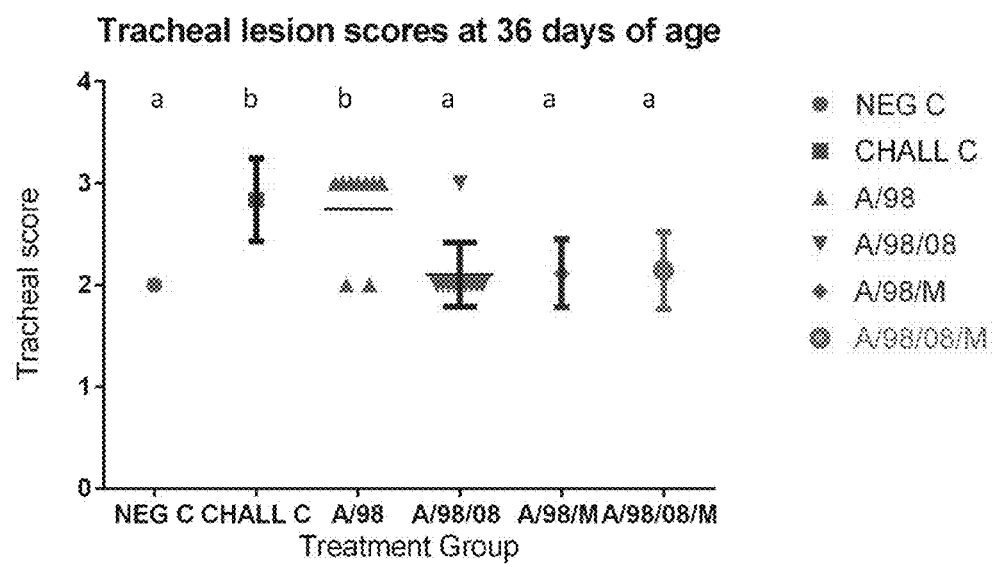

Vaccination challenge study. Clinical signs were not observed in the negative control group during the course of the study (FIG. 2). All tracheas (5/5) in the negative control group had minimal to mild lymphocytic infiltration in the lamina propria and scored 2 (FIG. 3). Most kidneys (5/6) in the negative control group had multifocal small lymphocytic infiltrates in the interstitium and scored 2, while one kidney did not have significant findings and scored 1.

In the unvaccinated-challenged group, conjunctivitis and moderate to severe airsacculitis was observed in 5 of the 6 birds (FIG. 2). The sixth bird had mild airsac. Broilers in this group had tracheitis with microscopic lesions consistent with IBV infection, and the lesions were more severe than the ones seen in the control group. Five tracheas scored 3 and one trachea scored 2 (FIG. 3). Mild and nonspecific renal tubular necrosis was seen in 3/6 kidneys, which could possibly be caused by acute dehydration or acute IBV infection. Four kidneys scored 3 and two kidneys scored 2. Ciliostasis evaluation found that birds in the unvaccinated and challenged group had ciliostatsis scores of 4, indicating less than 25% of cilia intact on the scale described by Cook (Cook et al., 1999, *Avian Pathology*; 28:477-485).

Birds in the Ark/GA98 group exhibited conjunctivitis in 2/9 birds and one bird had rales (FIG. 2). However the tracheal lesion score for this group was statistically higher than the negative controls and not statistically different from the unvaccinated challenged birds (FIG. 3).

Only 1/10 birds in the Ark/GA98/Mass group had conjunctivitis and 1/10 had mild airsac (FIG. 2). No significant difference was observed in the tracheal lesion score between this group and the negative controls, Ark/GA98/08 and Ark/GA98/08/Mass groups (FIG. 3).

Birds in the Ark/GA98/GA08 group did not have airsacculitis but at least 1/10 birds in the group had rales or conjunctivitis (FIG. 2). The majority of the tracheas in this group had tracheitis consistent with IBV infection, although lesion scores were not significantly different when compared to the negative control group (thirteen tracheas scored 2 and one trachea scored 3), Ark/GA98/Mass, or Ark/GA98/08/Mass (FIG. 3).

Only the group vaccinated with the Ark/GA98/GA08 and boosted with Ark/GA98/Mass combination had birds without airsacculitis. The tracheas in this group had lesions consistent with IBV infection, although lesion scores were not significantly different than the negative control group (one trachea scored 3 and six tracheas scored 2), Ark/GA98/GA08 or Ark/GA98/Mass (FIG. 3).

Figure 4:
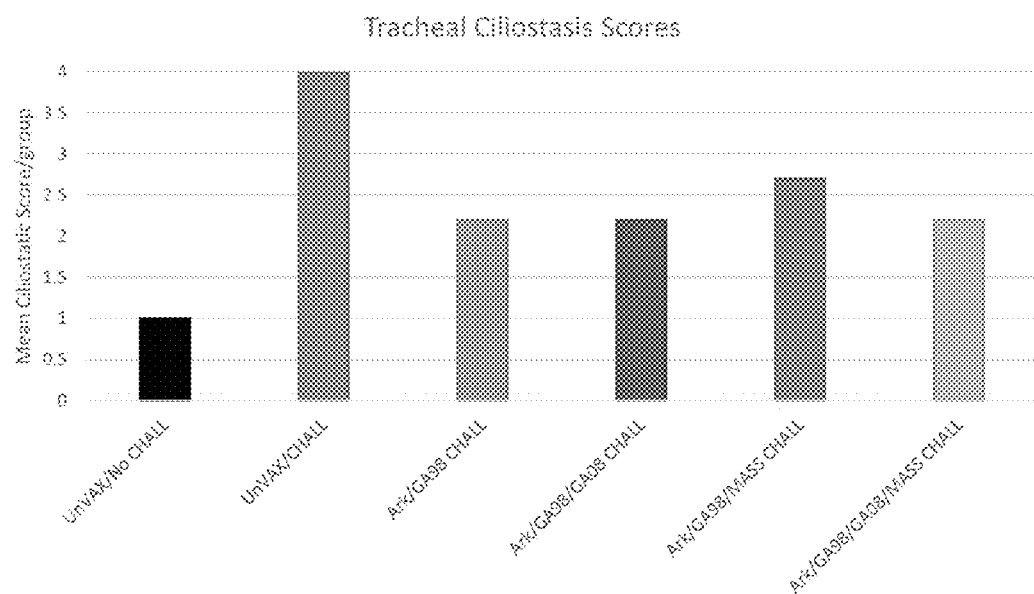

No significant differences were observed in ciliostatis scores between vaccinated/challenged groups. Scores for these groups ranged from 2.2 to 2.7 as compared to a score of 1, indicative of 75%-99% of cilia intact and beating normally, as observed in the unvaccinated and unchallenged negative control group. All vaccinated/challenged groups had significantly higher scores compared to the negative control group and the Ark/GA98, Ark/GA98/08 and Ark/GA98/08/Mass had significantly lower scores compared to the unvaccinated/challenged birds (FIG. 4).

A significant decrease in viral load, as measured by higher Ct values, was observed in all 4 vaccinated groups compared to the unvaccinated and challenged group. In addition, all 4 vaccinated group had a significantly higher viral load compared to the unvaccinated/unchallenged group (FIG. 5). The Ark/GA98 vaccinated group had a significantly higher viral load compared to the Ark/GA98/GA08 group but not to the Ark/GA98/Mass or Ark/GA98/GA08/Mass groups.

Discussion

Both the initial pathogenicity study, as well as the vaccination challenge, study establish that the GA13 variants are pathogenic in commercial broiler chickens and reproduce a sudsy airsacculitis with mild clinical signs similar to that seen in the field. Notably, gross necropsy findings as well histopathologic evaluation seem to indicate that this virus is primarily respirotropic despite the fact that its closest genetic relationship is with the two nephropathogenic variants previously isolated in PA. This is furthered supported by the ciliostasis evaluation which demonstrated a dramatic effect of this virus on the health and motility of tracheal cilia in unvaccinated chickens. While vaccination, even with serologically unrelated serotypes, does appear to decrease some clinical signs of disease it should be emphasized however that at least 10% of birds in all vaccinated groups still exhibited either clinical signs or gross lesions despite having received two full dose vaccinations administered by eyedrop and raised in ideal housing conditions; thus indicating that current vaccines do not provide full protection and may be inadequate in situations where vaccine coverage would be less than 100% and under more challenging field conditions. This is further supported by the Ct values observed, which indicate while vaccination does decrease the amount of viral genome present, it does not eliminate viral replication even in fully vaccinated subjects that received multivalent vaccinations at day of hatch followed by a boost at 17 days. Notably however, the vaccinated group that received Ark/GA98/GA08 at day of hatch and boosted with Ark/GA98/Mass at 17 days had the highest and most closely clustered Ct values of any vaccinated group. Whether or not this would translate into increased protection under field conditions is not known. Additional studies using larger groups may provide more support for inclusion of GA08 or Mass to current vaccination programs. Of course, the best protection would be achieved by a closely matched vaccine, but this is not always practical since commercial vaccines don't exist for IBV variant.

In conclusion, this example demonstrates the following. GA13 reproduces respiratory clinical disease seen in field cases. IBV viral genome reduced in vaccinated groups. Experimentally, addition of Mass and/or GA08 reduced gross lesions and tracheal pathology despite lack of genetic relatedness. And, serotype specific IBV vaccines typically provide the best option for protection and currently no commercial vaccine is available for the GA13 variant.

Example 2

Molecular Characterization of IBV GA13 Isolate 103505 Kd E3

The S1 subunit of the spike gene for a representative IBV GA13 isolate (103505 Kd E3) was sequenced. The following full-length S1 glycoprotein (IBV S1) nucleic acid sequence (SEQ ID NO:1) was obtained for IBV GA13 isolate 103505 Kd E3 (original tissue=kidney; $3^{rd}$ embryo passage).

(SEQ ID NO: 1)
ATGTCGGTAATACCTCTTTTGCTAGTGACTCTTTTGTTTGCACTATGTA

GTGCTGCTTTGTATGATAATGATTCTTTCGTTTACTACTACCAAAGTGC

CTTCAGACCATATGATGGCTGGCATTTACATGGAGGTGCTTATGAAGTT

ATTAATACTACTCAGGAATTTAATAATGCAGGTTTAAATTCTGAATGTA

CTGCTGGTGCCATTTCTTGGAGTAAGAATTTTTCTGCTGCTTCTGTAGC

CATGACTGCACCATATAATGGTATGTCGTGGTCTGTTCAGCAATTTTGC

ACGGCGCACTGTAATTTTACTTATTTTACAGTGTTTGTTACACATTGTT

ATAAGCGCGGAGTTGGCACGTGTCCTTTAACAGGTATGATTCCACAAAA

```
CCAAATCCGCATTTCTGCTATGAGAAGCGGTAGTGCTCCCCCGGATCTT

TTTTACAATTTAACAGTTCCTGTGACTAAATATCCTTCATTTAAGTCAC

TCCAATGTGTTAATAATCAAACGTCTGTATATTTAAATGGTGATCTTGT

TTTTTCATCTAATGAGACTATAGATGTTTCAGGTGCAGGTGTTCATTTT

AAAGCTGGTGGACCCATAACCTATAAAGTTATGAGAGAAGTTAAAGCCC

TGGCTTATTTTGTTAATGGTACCGCACAAGATGTCATTTTGTGCGATGG

TACACCCAGAGGTTTGTTAGCATGCCAATATAATACTGGCAATTTTACA

GATGGCTTCTATCCTTTTACTAATAGTAGTTTAGTTAAGGAAAAGTTTA

TTGTCTATCGTGAGAATAGTGTTAACGCCACTTTGGTTTTACATAATAT

TACGTTTTTTAATGAGACTAGTGCACCACCTGCCGGCGGTGATATTAGT

GCTATATTTCCAACTTATCAAATGGTAACAGCTCAGAGTGGTTATTATA

ATTTTAATTTCTCATTTCTGAGTGGTTTTGTTTATAAGGTAAGTGATTT

TATGTATGGGTCTTACCACCCAAAGTGTAATTTTAGACCAGAAAATCTT

AATAATGACCTCTGGTTTAATTCACTCTCAATCTCACTTGCTTATGGCC

CACTACAAGGGGCTGTAAGCAGTCGGTTTTTAATGGTAGAGCAACGTG

TTGTTATGCTTATTCATACAACGGTCCTCATGCTTGTAAAGGTGTCTAT

CGAGGTCAGTTACAACAATATTTTGAATGTGGGTTGCTAGTTTATATTA

CTAAGAGCGATGGCTCTCGTATACAAACAGCAACAAAAGCACCTGTAGT

AACTACAAATTTTTATAATAACATCACTTTAGATAGGTGTGTTGATTAT

AACATATATGGCAGAGTAGGCCAAGGTTTTATAACTAATGTAACTGACT

CAACTGCTGATTATAATTATTTAGCAGATGGAGGGTTAGCTATTTTAGA

CACATCAGGTGCTATAGACATCTTCGTTGTACAAGGTGAATATGGCCTT

AATTTTTATAAGGTTAATCCTTGCGAAGATGTTAATCAGCAGTTTGTAG

TTTCTGGTGGTAAGTTAGTAGGTGTTCTTACTTCACGTAATGAAACTGA

TTCTCAGTTCTTGAGAACCAGTTTTACATTAAACTCACTAATGAAACA

CATCG
```

The following full length S1 glycoprotein (IBV S1) amino acid sequence (SEQ ID NO:2) for the IBV GA13 isolate 103505 Kd E3 (original tissue=kidney; 3rd embryo passage) was deduced from the nucleotide sequence SEQ ID NO:1. (Also referred to as GA-103505 KdE3-2013 IBVS1 in the phylogenetic tree shown in FIG. 1).

```
                                              (SEQ ID NO: 2)
MSVIPLLLVTLLFALCSAALYDNDSFVYYYQSAFRPYDGWHLHGGAYEV

INTTQEFNNAGLNSECTAGAISWSKNFSAASVAMTAPYNGMSWSVQQFC

TAHCNFTYFTVFVTHCYKRGVGTCPLTGMIPQNQIRISAMRSGSAPPDL

FYNLTVPVTKYPSFKSLQCVNNQTSVYLNGDLVFSSNETIDVSGAGVHF

KAGGPITYKVMREVKALAYFVNGTAQDVILCDGTPRGLLACQYNTGNFT

DGFYPFTNSSLVKEKFIVYRENSVNATLVLHNITFFNETSAPPAGGDIS

AIFPTYQMVTAQSGYYNFNFSFLSGFVYKVSDFMYGSYHPKCNFRPENL

NNDLWFNSLSISLAYGPLQGGCKQSVFNGRATCCYAYSYNGPHACKGVY

RGQLQQYFECGLLVYITKSDGSRIQTATKAPVVTTNFYNNITLDRCVDY

NIYGRVGQGFITNVTDSTADYNYLADGGLAILDTSGAIDIFVVQGEYGL

NFYKVNPCEDVNQQFVVSGGKLVGVLTSRNETDSQFLENQFYIKLTNET

H
```

Nucleotide alignment of IBV S1 sequences of the various GA13 isolates of Table 1 and other known IBV isolates (including known vaccine IBV strains and GA-08 (see WO 2009/143332 and U.S. Pat. No. 8,679,504, each of which are hereby incorporated by reference in their entirety) was performed. IBV GA13 isolate GA-103505 KdE3-2014 IBVS1 (SEQ ID NO:1) was used as the reference sequence. This analysis of full length nucleotide sequences of IBV S1 genes of the various IBV isolates is as presented in Example 2 of U.S. Provisional Patent Application Ser. No. 62/028,435 (filed Jul. 24, 2014), which is hereby incorporated by reference in its entirety.

Example 3

Attenuation of IBV Isolates

A representative isolate of the newly described GA13 serotype of infectious bronchitis virus GA13, PDRC accession number 103505, was serially passaged in specific pathogen free (SPF) embryos for the purpose of attenuating the virus to serve as a master seed for a live attenuated vaccine. Procedures similar to those described in WO 2009/143332 and U.S. Pat. No. 8,679,504 were used. To date, the virus has been passaged more than 86 times in SPF embryos. Identity testing at passages 12, 17, 22, 37, 42, 52, 57, 62, and 86 confirm the identity of the passaged virus to be GA13.

The S1 subunit of the spike gene for the attenuated IBV GA13 103505KdE86 isolate was sequenced. The following full-length S1 glycoprotein (IBV S1) nucleic acid sequence (SEQ ID NO:3) was obtained for attenuated isolate IBV GA13 103505KdE86 master seed virus (MSV).

```
                                              (SEQ ID NO: 3)
ATGTCGGTAATACCTCTTTTGCTAGTGACTCTTTTGTTTGCACTATGTA

GTGCTGCTTTGTATGATAATGATTCTTTCGTTTACTACTACCAAAGTGC

CTTCAGACCATATGATGGCTGGCATTTACATGGAGGTGCTTATCAAGTT

ATTAATACTACTCAGGAATTTAATAATGCAGGTTTAAATTCTGAATGTA

CTGCTGGTGTCATTTCTTGGAGTAAGAATTTTTCTGCTGCTTCTGTAGC

CATGACTGCACCATATAATGGTATGTCGTGGTCTGTTCAGCAATTTTGC

ACGGCGCACTGTAATTTTACTTATTTTACAGTGTTTGTTACACATTGTT

ATAAGCGCGGAGTTGGCATGTGTCCTTTAACAGGTATGATTCCACAAAA

CCAAATCCGCATTTCTGCTATGAGAAGCGGTAGTGCTCCCCCGGATCTT

TTTTACAATTTAACAGTTCCTGTGACTAAATATCCTTCATTTAAGTCAC

TCCAATGTGTTAATAATCAAACGTCTGTATATTTAAATGGTGATCTTGT

TTTTTCATCTAATGAGACTATAGGTGTTTCAGGTGCAGGTGTTCATTTT

AAAGCTGGTGGACCCATAACCTATAAAGTTATGAGAGAAGTTAAAGCCC

TGGCTTATTTTGTTAATGGTACCGCACAAGATGTCATTTTGTGCGATGG

TACACCCAGAGGTTTGTTAGCATGCCAATATAATACTGGCAATTTTACA

GATGGCTTCTATCCTTTTACTAATAGTAGTTTAGTTAAGGAAAAGTTTA
```

-continued
```
TTGTCTATCGTGAGAATAGTGTTAACGCCACTTTGGTTTTACATAATAT

TACGTTTTTTAATGAGACTAGTGCACCACCTGCCGGCGGTGATATTAGT

GCTATATTTCCAACTTATCAAATGGTAACAGCTCAGAGTGGTTATTATA

ATTTTAATTTCTCATTTCTGAGTGGTTTTGTTTATAAGGTACGTGATTT

TATGTATGGGTCTTACCACCCAAAGTGTAATTTTAGACCAGAAAATCTT

AATAATGACCTCTGGTTTAATTCACTCTCAATCTCACTTGCTTATGGCC

CACTACAAGGGGCTGTAA GCAGTCGGTTTTTAATGGTAGAGCAACGT

GTTGTTATGCTTATTCATACAACGGTCCTCATGCTTGTAAAGGTGTCTA

TCGAGGTCAGTTACAACAATATTTTGAATGTGGGTTGCTAGTTTATATT

ACTAAGAGCGATGGCTCTCGTATACAAACAGCAACAAAAGCACCTGTAG

TAACTACAAATTTTTATAATAACATCACTTTAGATAGGTGTGTTGATTA

TAACATATATGGCAGAGTAGGCCAAGGTTTTATAACTAATGTAACTGAC

TCAACTGCTGATTATAATTATTTAGCAGATGGAGGGTTAGCTATTTTAG

ACACATCAGGTGCTATAGACATCTTCGTTGTACAAGGTGAATATGGCCT

TAATTTTTATAAGGTTAATCCTTGCGAAGATGTTAATCAGCAGTTTGTA

GTTTCTGGTGGTAAGTTAGTAGGTGTTCTTACTTCACGTAATGAAACTG

ATTCTCAGTTTCTTGAGAACCAGTTTTACATTAAACTCACTAATAAA
```

The following full length S1 glycoprotein (IBV S1) amino acid sequence (SEQ ID NO:4) for attenuated isolate IBV GA13 isolate 103505KdE863 MSV was deduced from the nucleotide sequence SEQ ID NO:2.

```
                                              (SEQ ID NO: 4)
MSVIPLLLVTLLFALCSAALYDNDSFVYYYQSAFRPYDGWHLHGGAY

QVINTTQEFNNAGLNSECTAGVISWSKNFSAASVAMTAPYNGMSWSV

QQFCTAHCNFTYFTVFVTHCYKRGVGMCPLTGMIPQNQIRISAMRSG

SAPPDLFYNLTVPVTKYPSFKSLQCVNNQTSVYLNGDLVFSSNETIG

VSGAGVHFKAGGPITYKVMREVKALAYFVNGTAQDVILCDGTPRGLL

ACQYNTGNFTDGFYPFTNSSLVKEKFIVYRENSVNATLVLHNITFFN

ETSAPPAGGDISAIFPTYQMVTAQSGYYNFNFSFLSGFVYKVRDFMY

GSYHPKCNFRPENLNNDLWFNSLSISLAYGPLQGGCKQSVFNGRATC

CYAYSYNGPHACKGVYRGQLQQYFECGLLVYITKSDGSRIQTATKAP

VVTTNFYNNITLDRCVDYNIYGRVGQGFITNVTDSTADYNYLADGGL

AILDTSGAIDIFVVQGEYGLNFYKVNPCEDVNQQFVVSGGKLVGVLT

SRNETDSQFLENQFYIKLTNK.
```

FIG. 6 shows the alignment of the full-length S1 glycoprotein (IBV S1) nucleic acid sequence of the IBV GA13 isolate 103505 Kd E3 (SEQ ID NO:1) compared with the full-length S1 glycoprotein (IBV S1) nucleic acid sequence of the attenuated IBV GA13 103505KdE86 isolate (SEQ ID NO:3). IBV GA13 isolate GA-103505 KdE3 was used as the reference sequence. Dots indicate nucleotides that match; sequence; letters represent nucleotides differing from the reference isolate; and dashes represent nucleotide deletions.

FIG. 7 shows the alignment of the deduced full-length S1 glycoprotein (IBV S1) amino acid sequence of the IBV GA13 isolate 103505 Kd E3 (SEQ ID NO:2) compared with the deduced full-length S1 glycoprotein (IBV S1) amino acid sequence of the attenuated IBV GA13 103505KdE86 isolate (SEQ ID NO:4). IBV GA13 isolate GA-103505 KdE3 was used as the reference sequence. Dots indicate nucleotides that match; sequence; letters represent nucleotides differing from the reference isolate; and dashes represent nucleotide deletions.

Changes in the full-length S1 glycoprotein (IBV S1) amino acid sequence of the attenuated IBV GA13 103505KdE86 isolate (SEQ ID NO:4) in comparison to the full-length S1 glycoprotein (IBV S1) amino acid sequence of the IBV GA13 isolate 103505 Kd E3 (SEQ ID NO:2) include the change from an glutamic acid (Glu; E) to a glutamine (Gln; Q) at position 48, an alanine (Ala; A) to a valine (Val; V) at position 69, a threonine (Thr; T) to a methionine (Met; M) at position 121, an aspartic acid (Asp; D) to a glycine (Gly; G) at position 188, and a serine (Ser; S) to an arginine (Arg; R) at position 325.

Example 4

GA13 E86 MSV Safety Test Results

Eighty, 1-day-old commercial broilers were obtained from the Fieldale Farms hatchery in Stephens County and transported to PDRC. Two groups of 25 and one group of 20 chicks were placed in forced air, positive pressure, Horsfall isolation units upon arrival. One group of 25 chicks was inoculated via eyedrop with GA-13 IBV E86 MSV (X) at $10^{5.5}$ $EID_{50}$ per bird while the second group of 25 chicks was inoculated intratracheally with $10^{5.5}$ $EID_{50}$ per bird. The 20 chicks in the 3rd group were kept as negative controls. The remaining 10 chicks were bled for IBV ELISA (IDEXX). Birds were monitored twice daily for clinical signs. On day 21, birds were euthanized and necropsied. Birds were evaluated for clinical signs and macroscopic lesions. Tracheas were collected for histopathological evaluation and scoring.

Results

The IBV GMT for the 10 day-of-hatch serum samples submitted was 1641 (CV 62.6) [Reference GPLN 10697600]. No clinical signs were observed in any of the groups during the 21 days following inoculation. A single mortality occurred in one bird from the negative control group due. No specific cause was related to this event. Macroscopic lesions observed on day 21 were limited to mild airsacculitis in two groups, 3/20 birds in the negative control group and 4/25 birds in the eyedrop group. The intratracheally inoculated group did not have any airsac in the 25 remaining birds.

Histological evaluation and scoring of tracheal rings from each group was performed. The mean tracheal score for each group is listed in FIG. 8. FIG. 8 shows mean tracheal lesion scores at 21 days of age and post-inoculation for groups 1) NEG=negative controls, 2) birds administered GA13 E86 MSV at $10^{5.5}$ $EID_{50}$ via eyedrop per bird and 3) birds administered GA13 E86 MSV intratracheally at $10^{5.5}$ $EID_{50}$ per bird. Tracheal scores are based on a 4 point system, 1-4 where a score of 1 may include=Normal, no inflammatory cells, cilia is present, goblet cells or mucous glands are present with little or no mucous in the lumen, score of 2 may include=epithelial hyperplasia, presence of inflammatory cells, deciliation, mucous in the lumen, increased numbers of goblet cells or mucous glands, score of 3 may include=any type of necrosis, can have hemorrhage associated with necrosis or not, inflammation present, and score of 4 may include=any amount of ulceration (no matter the cause), can have hemorrhage associated with ulcer or not.

As shown in this example, the GA13 E86 MSV was found to be safe at the 10× dose in day-old commercial broilers inoculated by the eyedrop or trachea. No clinical signs were observed throughout the 21 day trial period in any of the groups. Mild airsac was observed in 3/20 and 4/25 of the negative control and eyedrop groups, respectively. Due to the mild nature of the airsac, it appears to be a result of housing in isolation units as the intratracheally inoculated birds did not exhibit any airsac. Tracheal lesion scores were higher in both GA13 E86 IBV inoculated groups with average scores of 1.9 and 1.95 for the eyedrop and intratracheally inoculated groups, respectively, compared to 1.4 score for the negative controls. This is not unexpected as vaccine viruses do cause an inflammatory response following administration. This response did not progress to necrosis or ulceration over the course of the 21 days. 9 CFR states that a vaccine is considered safe if no more than 2 birds out of 25 fail the 10× dose. Based on the results from this study, the GA13 E86 MSV is considered safe, since no clinical signs were observed in any of the groups and since mild airsac was the only macroscopic lesion observed in a few birds in both the negative controls and eyedrop group but absent in the IT group.

Example 5

Attenuated GA13 Back-Passage Studies

The final results for 10 back-passages are described in this example. The goal of this example was to determine if the attenuated GA13 vaccine would revert pathogenic during successive passages in naïve birds. Non-vaccinated, day of hatch commercial chicks were provided by Fieldale Farms and housed in Horsfall Bauer FAPP (forced air, positive pressure) isolation units at PDRC.

Experimental Approach

The attenuated GA13 IBV was back-passaged in day-of-hatch commercial broiler chicks provided by Fieldale Farms. For the initial passage (VAX), 15 day-of-hatch chicks were inoculated via eye drop with the attenuated GA13 at $10^{4.5}$ $EID_{50}$/bird. The negative control group (n=10) was inoculated with 50 μl of sterile PBS for the first passage (VAX NEG). At 7 days post inoculation, tracheal swabs were collected from 5 birds in each group and pooled (by treatment group) in sterile tryptose phosphate broth for use in the next bird passage, RT-PCR for IBV detection and virus isolation. Birds were euthanized and tracheal sections collected and fixed in formalin per group for histological evaluation and scoring. Remaining birds in each group were monitored twice daily for clinical signs up to 21 days-of-age. At 21 days-of-age birds were euthanized, post mortem examination was performed and clinical signs noted (see Table 3, Necropsy 21 doa).

For BP#1-10, 50 μl of the 7 day swab supernatant from 1) GA13 VAX or BP and 2) negative controls (VAX NEG or BP1-10 NEG) was used to inoculate the next respective group of chicks via 50 μl eye drop.

Sample Testing

Serology. Serum was collected from day-of-hatch chicks and IBV ELISA performed at GPLN (Table 3).

TABLE 3

IBV ELISA geometric mean titers (GMT) from day-of-hatch chicks (n = 5).

| Group | GMT | GPLN Case Number |
| --- | --- | --- |
| GA13 vaccinated | 963 | 10712699 |
| BP1 | 803 | 10712666 |
| BP2 | 1406 | 10712668 |
| BP3 | 2173 | 10712670 |
| BP4 | 691 | 10712671 |
| BP5 | 801 | 10712672 |
| BP6 | 2862 | 10724256 |
| BP7 | 1049 | 10724258 |
| BP8 | 1196 | 10724259 |
| BP9 | 2112 | 10724261 |
| BP10 | 2544 | 10724255 |

Virus isolation and RT-PCR. Virus isolation and reverse transcription PCR (RT-PCR) for IBV was performed on the tracheal swab supernatants collected at 7 days of age. Sequencing was performed for confirmation of IBV identity (Table 4).

TABLE 4

GA13 back-passage experimental groups. Virus isolation and RT- PCR results from tracheal swabs collected at 7 days of age (d.o.a.) from GA13 vaccination (VAX) or back-passed birds (BP1-10). Clinical signs and lesions noted at 21 days of age from Negative controls (NEG = no vaccine) and GA13 VAX and BP1-10 birds are also summarized for each passage.

| PDRC Case # | Chick Passage | Tracheal swabs 7 d.o.a. | | Necropsy - 21 d.o.a. | |
| --- | --- | --- | --- | --- | --- |
| | | RT-PCR/Seq | VI/Seq | NEG | GA13 |
| 108218 | VAX | + (GA13) | + (GA13) | 5/5 NCS, NLS | 3/10 mild snick; 10/10 NLS |
| 108335 | BP1 | + (GA13) | + (GA13) | 5/5 NCS, NLS | 1/10 bacterial infection* |
| 108344 | BP2 | + (GA13) | + (GA13) | 5/5 NCS, NLS | 10/10 NCS, NLS |
| 108365 | BP3 | + (GA13) | + (GA13) | 5/5 NCS, NLS | 10/10 NCS, NLS |
| 108531 | BP4 | + (GA13) | + (GA13) | 5/5 NCS, NLS | 10/10 NCS, NLS |
| 108592 | BP5 | + (GA13) | + (GA13) | 4/4 NCS, NLS | 10/10 NCS, NLS |
| 108604 | BP6 | + (GA13) | + (GA13) | 5/5 NCS, NLS | 10/10 NCS, NLS |
| 108747 | BP7 | + (GA13) | + (GA13) | 5/5 NCS, NLS | 10/10 NCS, NLS |
| 109229 | BP8 | + (GA13) | + (GA13) | 5/5 NCS, NLS | 10/10 NCS, NLS |
| 109318 | BP9 | + (GA13) | + (GA13) | 5/5 NCS, NLS | 10/10 NCS, NLS |
| 109436 | BP10 | + (GA13) | + (GA13) | 5/5 NCS, NLS | 10/10 NCS, NLS | d.o.a = days of age
NCS = no clinical signs
NLS = no macroscopic lesions
+ = positive for IBV by RT-PCR on tracheal swabs and virus isolation (VI) from tracheal swabs.
All RT-PCR positive samples were sequenced for IBV identity.
Seq = IBV S1 RT-PCR product nucleotide sequence
*= bacterial infection in this bird did not appear to be associated with GA13 vaccination as this bird had a retained yolk sac and was smaller than hatch mates.

Histopathology. Histological scoring on cross sections of tracheas was performed. Tracheal lesion scores for each back-passage are summarized in FIG. 9. FIG. 9 shows mean tracheal lesion scores on fixed tracheal rings. Tracheal scores are based on a 4 point system, 1-4, where a score of 1 may include=Normal, no inflammatory cells, cilia is present, goblet cells or mucous glands are present with little or no mucous in the lumen, score of 2 may include=epithelial hyperplasia, presence of inflammatory cells, deciliation, mucous in the lumen, increased numbers of goblet cells or mucous glands, score of 3 may include=any type of necrosis, can have hemorrhage associated with necrosis or not, inflammation present, and score of 4 may include=any amount of ulceration (no matter the cause), can have hemorrhage associated with ulcer or not.

This example demonstrated the following. IBV GMTs for each group of day-of-hatch chicks ranged from 691-2862. All tracheal swabs collected at 7 d.o.a. from GA13 VAX and back-passaged (BP1-10) birds were positive for IBV by RT-PCR and GA13 identity confirmed by sequencing. Viable IBV was confirmed at 7 d.o.a. in all GA13 VAX and BP1-10 birds by virus isolation from tracheal swabs and GA13 identity confirmed by sequencing. Mild clinical signs were observed in 3/10 GA13 VAX birds at 21 days of age. No clinical signs were observed in GA13 back-passages 1-10. Tracheal lesion scores were highest in all GA13 VAX and BP1-10 groups compared to respective negative control groups for each passage. This is consistent with IBV vaccination. Tracheal lesion scores were highest (= to 3) in the GA13 BP3 group compared to the GA13 VAX and GA13 BP1-2 and 4-10 groups. Tracheal lesion scores of 3 have also been observed in Arkansas vaccination/challenge studies. No clinical signs or lesions were observed in the GA13 BP3 study so any tracheal impairment appears to have been resolved by 21 days of age. The GA13 attenuated vaccine was stable through 10 back-passages as evidenced through the absence of significant clinical signs and lesions.

The complete disclosure of all patents, patent applications, and publications, and electronically available material (including, for instance, nucleotide sequence submissions in, e.g., GenBank and RefSeq, and amino acid sequence submissions in, e.g., SwissProt, PIR, PRF, PDB, and translations from annotated coding regions in GenBank and RefSeq) cited herein are incorporated by reference. In the event that any inconsistency exists between the disclosure of the present application and the disclosure(s) of any document incorporated herein by reference, the disclosure of the present application shall govern. The foregoing detailed description and examples have been given for clarity of understanding only. No unnecessary limitations are to be understood therefrom. The invention is not limited to the exact details shown and described, for variations obvious to one skilled in the art will be included within the invention defined by the claims.

All headings are for the convenience of the reader and should not be used to limit the meaning of the text that follows the heading, unless so specified.

Sequence Listing Free Text

SEQ ID NO:1 Nucleotide sequence of the S1 subunit of the spike gene for IBV GA13 isolate 103505 Kd E3

SEQ ID NO:2 Amino acid sequence of the S1 subunit of the spike gene for IBV GA13 isolate 103505 Kd E3

SEQ ID NO:3 Nucleotide sequence of the S1 subunit of the spike gene of the attenuated IBV GA13 isolate 103505 Kd E86

SEQ ID NO:4 Amino acid sequence of the S1 subunit of the spike gene of the attenuated IBV GA13 isolate 103505 Kd E86

SEQ ID NO:5-6 Nucleotide Primers

What is claimed is:

1. An attenuated infectious bronchitis virus (IBV) GA13 isolate, wherein the attenuated IBV GA13 isolate comprises GA13 103505 Kd E86 deposited under ATCC Accession Number PTA-124038.

2. An attenuated infectious bronchitis virus (IBV) GA13 isolate, the attenuated IBV GA13 isolate comprising an S1 glycoprotein subunit comprising an amino acid sequence comprising at least about 95% sequence identity to SEQ ID NO: 4, wherein SEQ ID NO: 4 comprises the amino acid sequence of the S1 glycoprotein subunit of the attenuated IBV GA13 isolate GA13 103505 Kd E86 deposited under ATCC Accession Number PTA-124308.

3. The attenuated IBV GA13 isolate of claim 2, wherein the S1 glycoprotein subunit comprises any one, any two, any three, any four, or all five of the following amino acids residues:

a glutamine at position 48;
a valine at position 69;
a methionine at position 121;
a glycine at position 188; and/or
an arginine at position 325.

4. An attenuated infectious bronchitis virus (IBV) GA13 isolate, the attenuated IBV GA13 isolate comprising an S1 glycoprotein subunit encoded by a nucleotide sequence comprising at least about 95% sequence identity to SEQ ID NO: 3, wherein SEQ ID NO: 3 comprises the nucleotide sequence encoding the S1 glycoprotein subunit of the attenuated IBV GA13 isolate GA13 103505 Kd E86 deposited under ATCC Accession Number PTA-124308.

5. The attenuated IBV GA13 isolate of claim 1, wherein the attenuated IBV GA13 isolate is lyophilized.

6. A composition comprising the attenuated IBV GA13 isolate of claim 1.

7. The composition of claim 6, wherein the composition further comprises other viral material.

8. A method of producing an immune response to an IBV virus in poultry, the method comprising administering an effective amount of the composition of claim 6 to poultry.

9. The method of claim 8, wherein the composition is administered in the drinking water or by spraying the poultry's environment.

10. A method of producing an immune response to an IBV virus in poultry, the method comprising administering an effective amount of the composition comprising the attenuated IBV GA13 isolate of claim 3 to poultry.

11. The method of claim 10, wherein the composition is administered in the drinking water or by spraying the poultry's environment.

12. The attenuated IBV GA13 IBV isolate of claim 3, wherein the S1 glycoprotein subunit comprises an amino acid sequence comprising at least about 98% sequence identity to SEQ ID NO: 4.

13. The attenuated IBV GA13 isolate of claim 4, comprising an S1 glycoprotein subunit encoded by a nucleotide sequence comprising at least about 98% sequence identity to SEQ ID NO: 3.

14. The attenuated IBV GA13 isolate of claim 2, wherein the attenuated IBV GA13 isolate is lyophilized.

15. A composition comprising the attenuated IBV GA13 isolate of claim 2.

16. A method of producing an immune response to an IBV virus in poultry, the method comprising administering an effective amount of the composition of claim 15 to poultry.

17. The attenuated IBV GA13 isolate of claim 4, wherein the attenuated IBV GA13 isolate is lyophilized.

18. A composition comprising the attenuated IBV GA13 isolate of claim 4.

19. A method of producing an immune response to an IBV virus in poultry, the method comprising administering an effective amount of a composition comprising the attenuated IBV GA13 isolate of claim 12 to poultry.

* * * * *